(12) United States Patent
Ramachandran

(10) Patent No.: US 10,755,806 B2
(45) Date of Patent: *Aug. 25, 2020

(54) GRAPHICAL PRESENTATION OF MEDICAL DATA

(71) Applicant: QUEST DIAGNOSTICS INVESTMENTS INCORPORATED, Wilmington, DE (US)

(72) Inventor: Kavya Ramachandran, Herndon, VA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/177,970

(22) Filed: Nov. 1, 2018

(65) Prior Publication Data

US 2019/0074075 A1    Mar. 7, 2019

Related U.S. Application Data

(63) Continuation of application No. 15/674,042, filed on Aug. 10, 2017, now Pat. No. 10,169,538, which is a continuation of application No. 14/602,141, filed on Jan. 21, 2015, now Pat. No. 9,966,153, which is a continuation of application No. 11/532,093, filed on Sep. 14, 2006, now abandoned, which is a
(Continued)

(51) Int. Cl.
| | | |
|---|---|---|
| G16H 15/00 | (2018.01) | |
| G06F 3/0482 | (2013.01) | |
| G06F 16/901 | (2019.01) | |
| G16H 10/60 | (2018.01) | |
| G16Z 99/00 | (2019.01) | |
| G06F 19/00 | (2018.01) | |

(52) U.S. Cl.
CPC ........... G16H 15/00 (2018.01); G06F 3/0482 (2013.01); G06F 16/9024 (2019.01); G06F 19/00 (2013.01); G16H 10/60 (2018.01); G16Z 99/00 (2019.02)

(58) Field of Classification Search
CPC combination set(s) only.
See application file for complete search history.

(56) References Cited

U.S. PATENT DOCUMENTS 5,812,983 A    9/1998 Kumagai
9,466,050 B2 * 10/2016 Yee ..................... G06Q 10/10
(Continued)

OTHER PUBLICATIONS

Microsoft Corporation, Microsoft Office Excel, 2003, version 11.8316.8172 with service pack 3.

*Primary Examiner* — Motilewa Good Johnson
(74) *Attorney, Agent, or Firm* — Jon E. Gordon; Haug Partners LLP

(57) ABSTRACT

Methods and user interfaces are provided for the display of data comprising series of data over time, with particular application to medical laboratory results and prescriptions of medication. A user may view multiple results simultaneously in a single display, with the abilities to zoom the time scale in and out and to select the time period for which results are displayed. Multiple displayed items of data may be selected for simultaneous display along a common time axis in a zoomable graph, facilitating interpretation of relationships between and/or among data items.

6 Claims, 17 Drawing Sheets

Related U.S. Application Data continuation of application No. 11/324,134, filed on Dec. 29, 2005, now abandoned.

(56) References Cited

U.S. PATENT DOCUMENTS

| | | | |
|---|---|---|---|
| 9,966,153 B2* | 5/2018 | Ramachandran | G16H 10/60 |
| 10,169,538 B2* | 1/2019 | Ramachandran | G16H 10/60 |
| 2005/0265580 A1 | 12/2005 | Antonucci et al. | |
| 2013/0144653 A1 | 6/2013 | Poe | |
| 2015/0116333 A1 | 4/2015 | Harper | |
| 2015/0121279 A1 | 4/2015 | Huang | |
| 2016/0321399 A1* | 11/2016 | Ramachandran | G16H 10/60 |

* cited by examiner

Test Value: 111 MG/DL — 763
Reference Range: 65-109 — 770
Office ID: ARZ 000 4124 — 774
Order #: 0000113 — 775
Comments: — 780

Ordering Physician: Rodolfo Pena-Ariet — 776
Collection Date: 09/15/04 10:19 — 777
Accession #: diab_chol_300 — 778
Performing Lab: Eastern Labs - Tampa — 779

```
<message>
    <header>
        <sender-id>8675309069</sender-id>          866
        <recipient-id>7365000422</recipient-id>    868
        <message-id>000497521336</message-id>      870
        <subject>Patient Referral</subject>
        .
        .
    </header>
    <body>
        <text>Dear Dr. Thomas: I have referred to you the patient
we spoke of last week. I have attached the test results to this message
for your review. Please call me when you have time to discuss this.</
text>
    </body>
    <attachments>
        <attachment type="reference">    884
            60e79772bade4foc              882
        </attachment>
    </attachments>
    .
    .
</message>
```

864 = header block
874 = body block
880 = attachments block

FIG. 16

GRAPHICAL PRESENTATION OF MEDICAL DATA

CROSS-REFERENCE TO RELATED APPLICATIONS

This application is a continuation of U.S. patent application Ser. No. 15/674,042, filed 10 Aug. 2017 and titled "Graphical Presentation of Medical Data"; which is a continuation of U.S. patent application Ser. No. 14/602,141, now U.S. Pat. No. 9,966,153, filed 21 Jan. 2015 and titled "Graphical Presentation of Medical Data"; which is a continuation of U.S. patent application Ser. No. 11/532,093, filed Sep. 14, 2006, and titled "Graphical Presentation of Medical Data"; which is a continuation of U.S. patent application Ser. No. 11/324,134, filed 29 Dec. 2005 and titled "Graphical Presentation of Medical Data"; all of which applications are incorporated herein by reference in their entirety.

BACKGROUND

Electronic Health Records

A number of things have driven the growth in all aspects of the health care industry of computerized systems providing Electronic Health Records (EHRs) and Electronic Medical Records (EMRs). (The term "EHR system" is used herein to refer to computerized systems that store, maintain, and/or provide EHRs. In other contexts, the term may have different significance.) For example, governmental regulation continues to move towards impelling the adoption of EHR systems. In addition, EHR systems reduce the chances of loss of patient records and mistakes in data entry and make delivery of health care more efficient, thereby offering the prospects of improving patient care while lowering its cost. Further, EHR systems may help ease the burden of paperwork that now afflicts the delivery of health care.

An EHR system may record and aggregate any type of data associated with health care, including, e.g., data about patients, including, e.g., their names, addresses, insurance coverage and/or other financial arrangements, health conditions, allergies, procedures undergone, and/or tests performed. Other recorded data may relate to, among other things, health care providers, payers, pharmacies, and/or employers.

An EHR system may comprise facilities for creating graphs of data, including patient data.

Electron data of any sort is associated with other data that describes it, provides context for it, associates it with other data, and/or otherwise signifies the meaning, significance, and/or one or more other attributes of the electronic data. This accompanying data is often called "metadata."

For example, in the medical field, an application may display the results of a blood test for cholesterol levels. The display may include data such as the levels of total cholesterol, HDLs, and LDLs, among other data. Some or all of this data may be associated with further data, such as the date of the test, the location where the blood sample was drawn, the identity of the laboratory ("lab") that analyzed the sample, the identity of the patient, and the identity of the practitioner who ordered the test, and this further data can be considered metadata. The appropriate characterization of data sometimes depends on the ways in which it is treated in computerized tiles, applications, and/or systems.

BRIEF SUMMARY

The invention relates to the visual representation of data as tables and/or graphs. More specifically, it involves display on an electronic display device of at least one table, with each table comprising at least one series of values over time. In an embodiment of the invention, the values are analytes measured in medical laboratory tests and/or prescriptions for medication.

The invention also involves the automatic generation and presentation of graphs, on which some or all values from at least one table are plotted against time. A graph according to an embodiment of the invention may comprise multiple values, e.g., of analytes and/or prescriptions, and may comprise the simultaneous presentation of multiple values that are measured against a plurality scales, using a plurality of units of measure.

According to an embodiment of the invention, multiple graphs may be presented simultaneously. In such an embodiment, the graphs may be aligned with one another so that they share a common time scale, facilitating correlation between one or more events plotted on one graph and one more other event plotted on the other graph. In an embodiment of the invention, two graphs may be so presented, with one graph presenting values of analytes and the other graph presenting data about medications.

An embodiment of the invention comprises a computerized method of presenting information graphically, comprising: presenting on an electronic display device a list comprising a plurality of series of one or more related data points, wherein each data point comprises a value and a date; in response to input from a user, selecting a first one or more of the plurality of series of the one or more related data points; in response to input from a user, selecting a second one or more of the plurality of series of the one or more related data points; in response to input from the user, presenting on the electronic display device a user interface display that comprises (a) a first graph that comprises a first horizontal axis indicating a time interval, a first vertical axis indicating a first range of values, and at least one set of symbols that correspond individually to one or more data points comprised by one or more of the first selected one or more series, wherein the horizontal placement of each symbol indicates the time associated with the corresponding data point, and the vertical placement of each symbol indicates the value associated with the corresponding data point, and (b) a second graph that comprises a second horizontal axis indicating a time interval, a second vertical axis indicating a second range of values, and at least one set of symbols that correspond individually to one or more data points comprised by one or more of the second selected one or more series, wherein the horizontal placement of each symbol indicates the time associated with the corresponding data point, and the vertical placement of each symbol indicates the value associated with the corresponding data point; wherein the first graph is presented adjacent to the second graph and either above it or below it, and the first horizontal axis and the second horizontal axis are aligned vertically so that any position indicating a time relative to the first horizontal axis indicates the same time relative to the second horizontal axis.

In a further embodiment, the first vertical axis is associated with a first unit of measurement; the first graph comprises a third vertical axis indicating a third range of values, which is associated with a second unit of measurement that is different from the first unit of measurement; each of the first one or more selected series of one or more data points is associated with either the first unit of measurement or the second unit of measurement; and each symbol is associated with the vertical axis that is associated with the same unit of measurement that the corresponding data point is associated with.

In a further embodiment, each data point that corresponds to a symbol comprised by the first graph comprises a result for an analyte in a laboratory test.

In a further embodiment, each data point that corresponds to a symbol comprised by the second graph comprises a prescription for and/or dispensing of medication.

An embodiment of the invention comprises a user interface to a computer system, displayed on an electronic display device, comprising: a first graph that comprises a first horizontal axis indicating a time interval, a first vertical axis indicating a first range of values, and at least one set of symbols that correspond individually to one or more data points comprised by one or more of a first one or more series, wherein the horizontal placement of each symbol indicates the time associated with the corresponding data point, and the vertical placement of each symbol indicates the value associated with the corresponding data point; a second graph that comprises a second horizontal axis indicating a time interval, a second vertical axis indicating a second range of values and at least one set of symbols that correspond individually to one or more data points comprised by one or more of the second selected one or more series, wherein the horizontal placement of each symbol indicates the time associated the corresponding data point, and the vertical placement of each symbol indicates the value associated with the corresponding data point; wherein the first graph is presented adjacent to the second graph and either above it or below it, and the first horizontal axis and the second horizontal axis are aligned vertically so that any position indicating a time relative to the first horizontal axis indicates the same time relative to the second horizontal axis.

In a further embodiment, the first vertical axis is associated with a first unit of measurement, the first graph comprises a third vertical axis indicating a third range of values, which is associated with a second unit of measurement that is different from the first unit of measurement, and each data point that is represented by a symbol comprised by the first graph is associated with either first vertical axis or the third vertical axis.

In a further embodiment, each data point that is represented by a symbol comprised by the first graph represents a result for an analyte in a laboratory test.

In a further embodiment, each data point that is represented by a symbol comprised by the second graph represents a prescription for and/or dispensing of medication.

An embodiment of the invention may be implemented in association with a computerized EHR system that comprises, among other patient care features, electronic lab test ordering, online delivery and viewing of lab results, and electronic eligibility checking and prescribing. An EHR system in association with which an embodiment of the invention can be implemented may provide patient care features that support some or all of a set of tasks comprising, among others:

ordering lab tests;
accessing and viewing lab results;
providing clinical insights at the time of ordering, delivering results, or both;
preparing and ordering drug prescriptions;
performing Pharmacy Benefit Manager (PBM) eligibility checks, including pharmacy coverage, PBM formulary, and patient medication history;
performing drug-to-drug interaction checking per prescription, as well as across a patient's active medications and medication history;
performing drug-allergy interaction checking per prescription;
communicating prescriptions to pharmacies and/or receiving requests from pharmacies for prescription refills;
managing clinical documents received from external systems;
communicating clinical data securely within and between physician offices;
viewing data by patient, user, and organization; analyzing patient data using various tools, including flowsheets, graphs, and informatics queries;
accessing a user-configurable inbox for both clinical and non-clinical data;
maintaining associations of physicians-to-provider organizations, physicians-to-payer plans, and physicians-to-specialties;
communicating with one or more labs to gain assistance in interpreting results;
communicating with one or more labs to order supplies; and
accessing information provided by one or more labs, such information comprising, for example, test dictionaries, lab manuals, and Patient Service Center (PSC) locations.

Such an EHR system may enable access to clinical data for patients in locations that may comprise a providers office, a hospital, and a provider's or patient's home and may provide encryption of data passed over networks comprising, for example, intranets or the Internet.

BRIEF DESCRIPTION OF THE DRAWINGS

The invention is illustrated in the figures of the accompanying drawings, which are meant to be exemplary and not limiting, and in which like references are intended to refer to like or corresponding things.

FIG. 8 depicts a user interface display adapted to creation of a new prescription according to an embodiment of an EHR system.

FIG. 10 depicts a user interface display that presents results of laboratory tests.

FIG. 12 depicts a user interface display that presents detailed laboratory results for an analyte and medications according to an embodiment of the invention.

FIG. 16 is an example of a partial representation of an electronic message as XML according to an embodiment of an EHR system.

DETAILED DESCRIPTION OF THE PREFERRED EMBODIMENTS

EHR Architecture

In the discussion that follows, the invention is discussed in connection with EHR systems. Such discussion is meant to illustrate the invention with respect to certain preferred embodiments, but it is to be understood that the discussion is illustrative and not limiting. It will be appreciated by one skilled in the art that nearly any time series of data may be graphed accordance with embodiments of the invention, not just medical or health-related data, and not only in connection with EHR systems.

Figure 1:
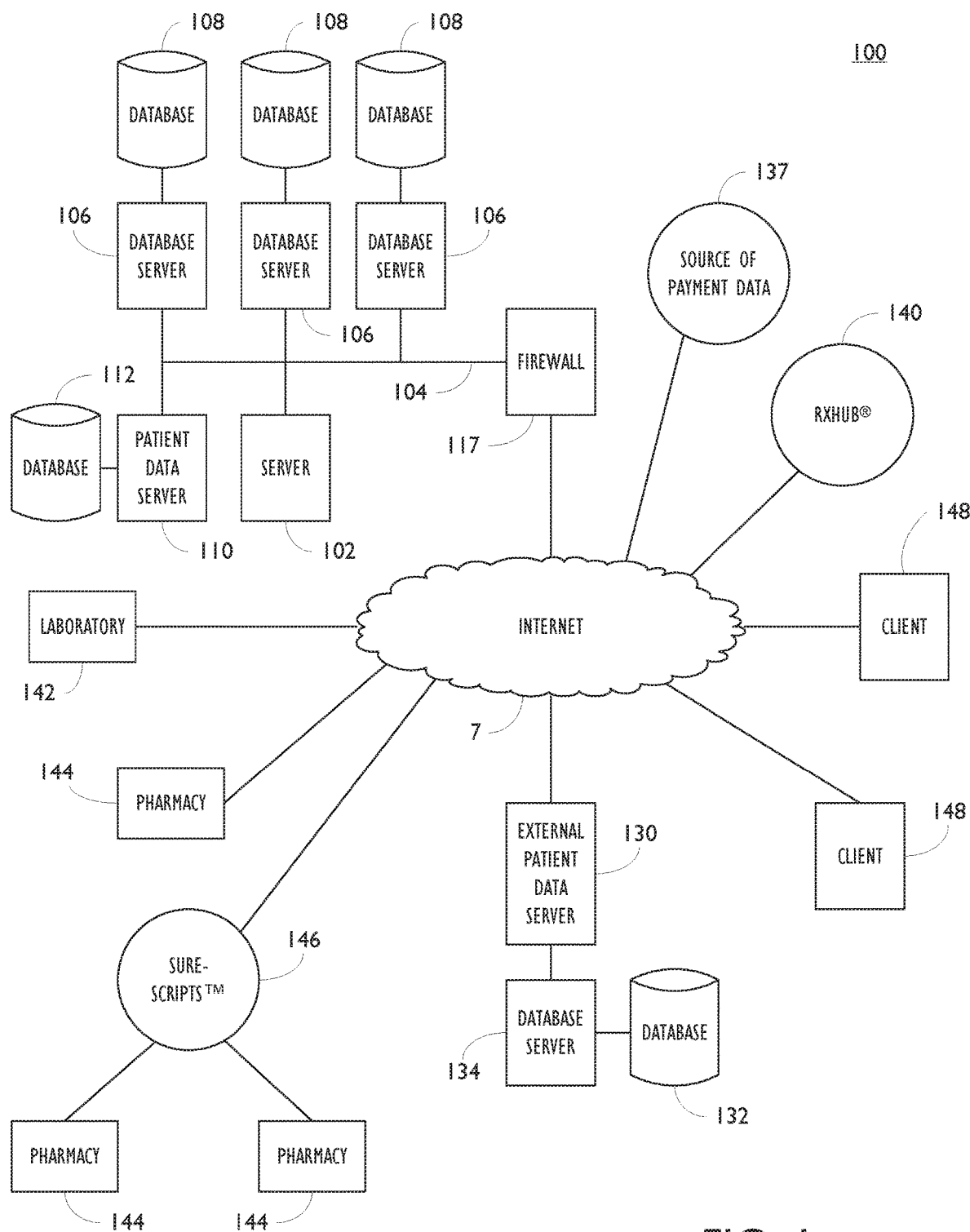
FIG. 1 schematically depicts networked computer systems suitable for implementing the invention.

FIG. 1 depicts an example of an architecture 100 suitable for use with an EHR system.

An EHR system itself may comprise computer software, software components, or both, executing on one or more servers 102. One or more interconnected local area networks 104 may connect the server 102 to one or more database servers 106, each of which provides access to one or more databases 108. The local area network may also contain one or more systems 110 that provide access to patients' medical histories, which may be stored in one or more local databases 112.

In the architecture depicted in FIG. 1, communication with other sources and consumers of information is achieved using the Internet 7. Access to the Internet may optionally be through one or more firewalls, gateways, and/or other security arrangements 117. Other means of communication may also be used instead of or in addition to the Internet, such as dial-up lines, dedicated leased lines, and private wide area networks (not pictured).

As depicted in FIG. 1, patient medical data may be stored in one or more databases 108, 112 and/or may be obtained from one or more external sources, such as server 130, which itself has access to a database 132 through a database server 134.

Information about health insurance and other forms of payment may be received electronically from one or snore sources 137. Prescription insurance data, which may comprise formulary data and rules, may also be received electronically from one or more sources, such as RxHub® 140.

An EHR system may be connected to one or more medical laboratories 142. Similarly, an EHR system may be connected to one or more pharmacies 144, directly and/or through a prescribing hub such as SureScripts™ 146.

Access to the EHR system is by one or more clients 148.

It will be appreciated by those skilled in the art that the architecture depicted in FIG. 1 is just one of many suitable for implementation of the invention. More than one component may be involved in performing one or more of the functions of the system, depending on the expected load and other factors. Functions depicted as being performed by separate components may in some implementations be performed by a single component, again, depending on the expected load and other needs of the system. Other configurations of servers and network topologies may work as well as those described here.

EHR system may be configured to restrict access to patients' medical records so that only authorized users have access to them. Such restrictions may be implemented, for example, to comply with laws and/or regulations concerning the protection of confidential medical data. Access to a particular patient's chart may therefore be restricted, e.g., to a practitioner, or to the practitioner and the practitioner's office staff, or those practitioners associated together within a specific medical practice, among many possibilities.

A user may be a member of one or more health care organizations, and an embodiment of an EHR system may limit users' interaction with the EHR system so that a user may be associated with only one such organization at a time. But such an EHR system may also allow a user to switch between those organizations as needed while remaining logged in to the application. If a user belongs to more than one organization, that user may have different permissions under each and may have access to different features of the embodiment. Depending on the EHR system, if each organization maintains a separate patient population, a user may not be able to access patients that exist within one organization while that user is logged in under a different organization.

EHR systems typically include means to authenticate the users. Well-known examples of such means include, but are not limited to, requiring a user: to log in with, e.g., a user name and password; to provide biometric information, e.g., via a fingerprint or retinal scan at the point of use; to provide a physical token or information provided by one, e.g., a temporarily valid access code; or some or all of these and/or other means. An embodiment may limit access to some or all of the functions of the embodiment, including the user interface depicted in FIG. 2 and/or other user interfaces, to successfully authenticated users or to subsets of them.

Figure 2:
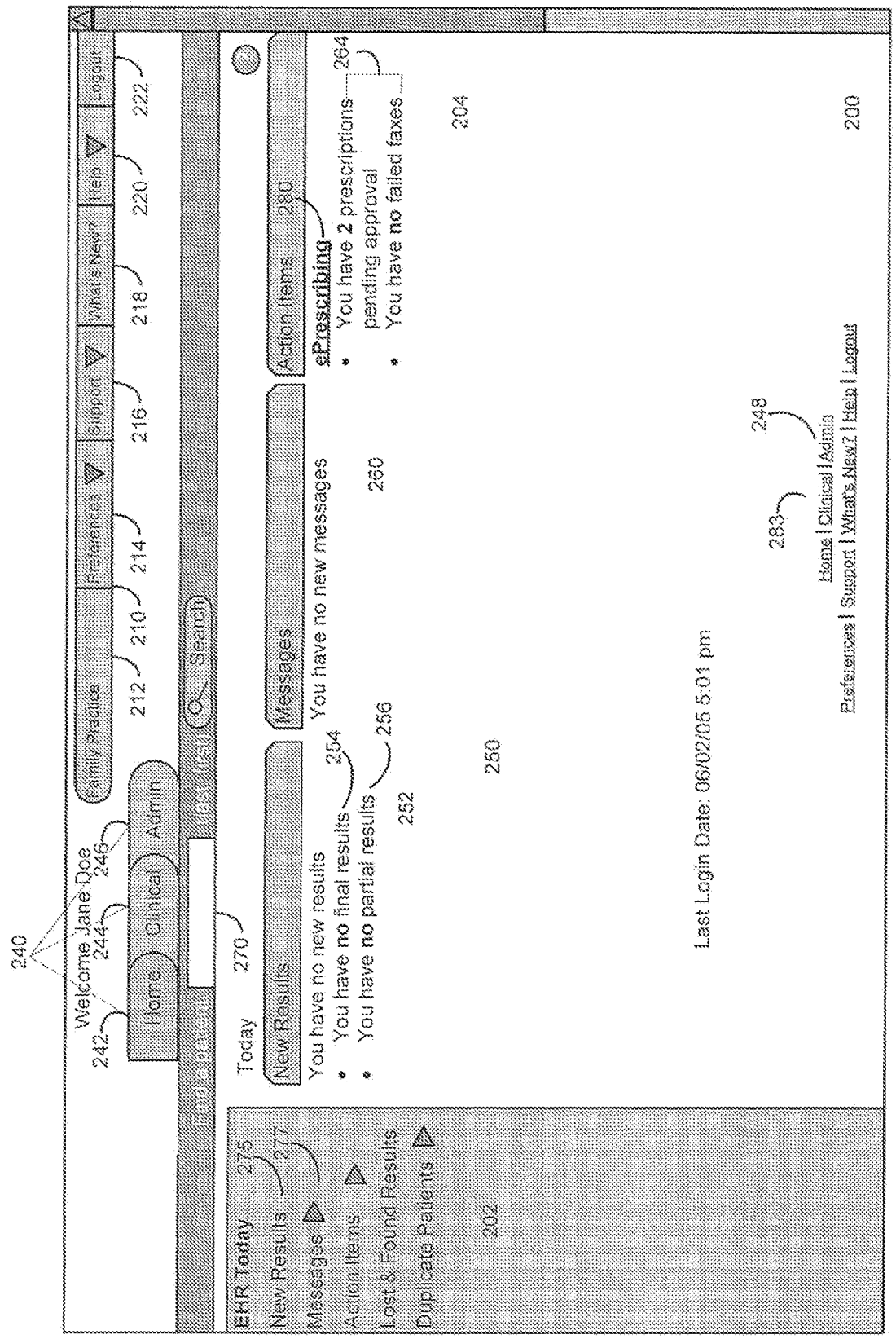
FIG. 2 depicts a user interface display adapted to navigate an embodiment of the invention.

FIG. 2 shows an initial (or "Home") screen 200 of an EHR system that may serve to allow a user to begin interacting with the system. This depicted screen 200 and those that follow may be used in connection with use of a thin client, such as a web browser. Other types of clients and/or other user interfaces (not pictured), with elements that correspond to those described herein as needed by the respective embodiments, may also be supported. EHR systems may support interaction with the user interface by well-known means for interacting with computer systems, which may comprise accepting user input via a pointing device such as a mouse and a keyboard and displaying output on a computer monitor.

The Home screen 200 may comprise certain navigation elements and cues common to some or all other user interface screens of an EHR system. Such common elements may comprise a function-specific navigation pane 202 that contains one or more links for accessing tasks related to the functional area currently being used and a function-specific content pane 204 displays content related to the task currently being performed.

Another such common element may be a navigation bar 210 that provides access to a number of general system functions. The navigation bar 210 displays the name of the organization or care site 212 currently associated with the user's interaction with the embodiment. If a user is associated with more than one organization or care site, the user may choose the one to associate with the interaction by clicking on this item.

Selecting the Preferences item 214 allows selection of one of several user preference options to see and possibly change. Such options may comprise, e.g., customizing user preference settings, specifying favorite states for pharmacy searches (discussed further below under the heading "ePrescribing"), anti changing the user's login password, among other things.

Selecting the Support item 216 allows selection of one of several user support options. Such options may comprise, e.g., sending feedback to system administrators, downloading and installing available product updates, and composing an email to a support team, among other things.

Selecting the What's New? item 218 causes display of information regarding new features of the system, if any.

Selecting the Help item 220 allows selection of user documentation to be displayed. Such documentation may comprise, e.g., online help and/or a comprehensive user manual, among other things. In a particular EHR system, the selected documentation may appear in a new window (not pictured) on a computer monitor.

Selecting the Logout item 222 logs the user out of the system. In an EHR system that provides user authentication, this may have the effect of requiring a user to authenticate anew before using the other features of the system.

An EHR system's user interface may comprise functional tabs 240 that provide direct access to functional areas of the system. In the system depicted, the Home tab 242 causes redisplay of the Home screen 200, which may be updated to display the latest information available. Selecting the Clinical tab 244 provides access to patient-related services, which may comprise, e.g., patient management, lab orders, lab results, and prescription orders. Selecting the Admin tab 246 provides access to administrative functions, in typical EHR systems, not all users have permission to use administrative functions.

Some or all navigation discussed in connection with the navigation bar 210, the functional tabs 240, and/or the links displayed in the function-specific navigation pane 202 may be provided or duplicated by hyperlinks elsewhere in the screen 200. FIG. 2 shows one example of such duplication in the form of a cluster 248 of hyperlinks in the function-specific content pane 204.

The Home screen 200 may provide access to the most commonly used facilities and information provided by the system. The function-specific content pane 204 displays a snapshot 250 of many of the activities occurring within the system that relate to the user and associated patients. Such a snapshot may comprise a count 252 of the new lab results that have been received, which may be further be broken down by whether those results are final 254 or partial 256, and may also show whether any of the results are abnormal. The snapshot may comprise the number 260 of new user messages in the user's inbox, the number 264 of prescriptions that are pending approval, and/or other information.

A user interface to an EHR system may allow direct return from other user interface screens to the Home screen 200, displaying snapshot 250, through clicking on the Home tab 242. When the Home screen 200 is already displayed, clicking on the Home tab 242 may, in some systems, cause the content to be updated to the latest information available.

The Home screen 200 may provide means to navigate the information and functions provided by an EHR system. Searching for a patient, for example, may be done by entering a name in Search field 270. Upon submission of the search, the system may cause information to be displayed regarding one or more matching patients or notification that no matches were found. Such information may appear in the function-sensitive content pane of Home screen 200, or it may appear in part of another screen such as patient selection screen 290, which is discussed below in connection with FIG. 3.

Other navigational facilities may exist. The function-specific navigation pane 202 links to other facilities and information provided by an EHR system. Depending on the system and the information currently available to the user, the links may include, for example, a "New Results" link 275 that causes the system to display new lab results, if any, and a "Messages" link 277 that provides access to user messaging functionality. Other links may be present for any other information and/or facility provided by the system.

Navigational facilities may also exist within the function-specific content pane 204. For example, in the Action Items area 264, there may be links to various items that require attention. FIG. 2 depicts such a link to ePrescribing functionality, which is discussed below.

Patient Management

Use of an EHR system may be organized conceptually around one or more aspects of EHRs or their management. For example, parts of the following discussion and the accompanying figures describe EHR systems that organize access to data around individual patients and the respective records that are associated with them. (Following historical practice, a collection of records for a single patient in an EHR system is sometimes referred to as the patient's "chart.") It will be obvious to one skilled in the relevant arts that EHR systems may be organized differently, e.g., around practitioners singly or in groups, payers, hospitals, or pharmacies without affecting the substance of the systems implemented or methods performed. It will be equally obvious that EHR systems may be organized around one or more such aspects and that such organization may or may not depend on a particular user's activity at the time of use.

EHR systems typically maintain EHRs for patients. In that regard, an EHR system may provide functionality comprising some or all of adding new patients, accessing patient charts, viewing patient data, and editing patient data.

EHR systems may vary in the way they provide for access to patient data and related functionality. From the Home screen 200 (FIG. 2), a user may select the Clinical tab 244 (or the Clinical hyperlink 283), which give access to functionality associated with clinical practice. Depending on the configuration of the system, that selection may lead directly to FIG. 3, which displays a patient selection screen 290.

Figure 3:
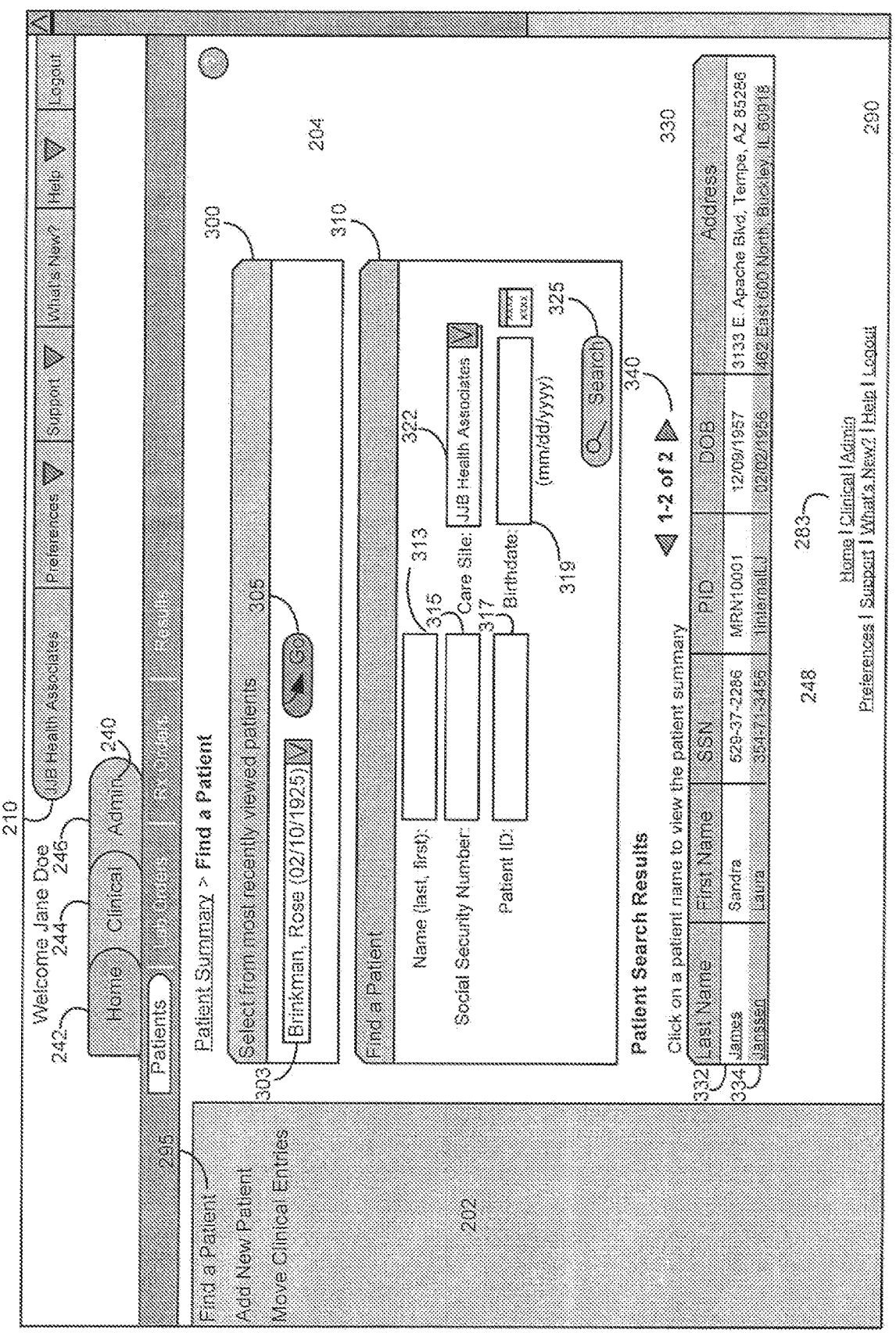
FIG. 3 depicts a user interface display adapted to search for a particular patient.

Some EHR systems may instead be configured to lead to different functionality upon selection of the Clinical tab 244 or hyperlink 283 (FIG. 2), and that functionality may then comprise links to screen 290 (FIG. 3). For example, a system may cause a link entitled "Find a Patient" 295 to appear in the function-sensitive navigation pane 202 when the Clinical tab 244 is selected. Selection of that link 295 then leads to display of screen 290.

Interfaces to one or more facilities for selecting a patient may comprise displays that appear in the function-sensitive content pane 204. One such interface is an area 300 containing a drop-down list 303 of the current user's most-recently-viewed patients. (An EHR system may let an administrator set a maximum number of patients that may appear in drop-down list 303.) Once the desired patient is selected, clicking the button labeled "Go" 305 then leads to display of records associated with that patient.

Another such interface is a search area 310 containing one or more controls that support searching for one or more patients. Depending on the system, one or more of the controls may comprise text entry controls that let a user specify, e.g., a patient's name 313, Social Security number 315, patient identification number 317, and birth date 319. Some EHR systems may permit searching based on partial matches, e.g., returning all records that merely begin with the text entered by the user or allowing "wildcard" characters in one or more search criteria that can be matched by any character or string of characters.

The search area 310 may comprise other types of control. For example, a drop-down list 322 may list one or more medical practices or health care sites or facilities with which a user has relationships (collectively referred to as "care sites"). Selecting a care site from the drop-down list 322 limits the search results to patients affiliated with that care site.

An EHR system may allow a user to execute a search after entering fewer than all possible search criteria. For example, an EHR system may support searching after the user has entered only the name "Johnson" in the Name text entry control 313. Other systems may require entry of data into some or all specific text entry controls before a search can be done.

After search criteria have been selected, the search may be executed by clicking the button labeled "Search" 325.

The search results area 330 lists patients whose records match the search criteria. The hyperlinks 332, 334 lead to display of records related to a selected patient. EHR systems may also provide means by which a user may proceed directly from the display of matching patients to one or more activities involving a selected patient, e.g., writing a prescription, ordering lab tests, or modifying a patient's medical history, among many possible options.

It may be desired to limit the number of matching patients that are displayed at once. In that case, a partial list may appear in the search results area 330, and a control 340 such as the one displayed may be provided to support moving backward and forward through the list.

Figure 4:
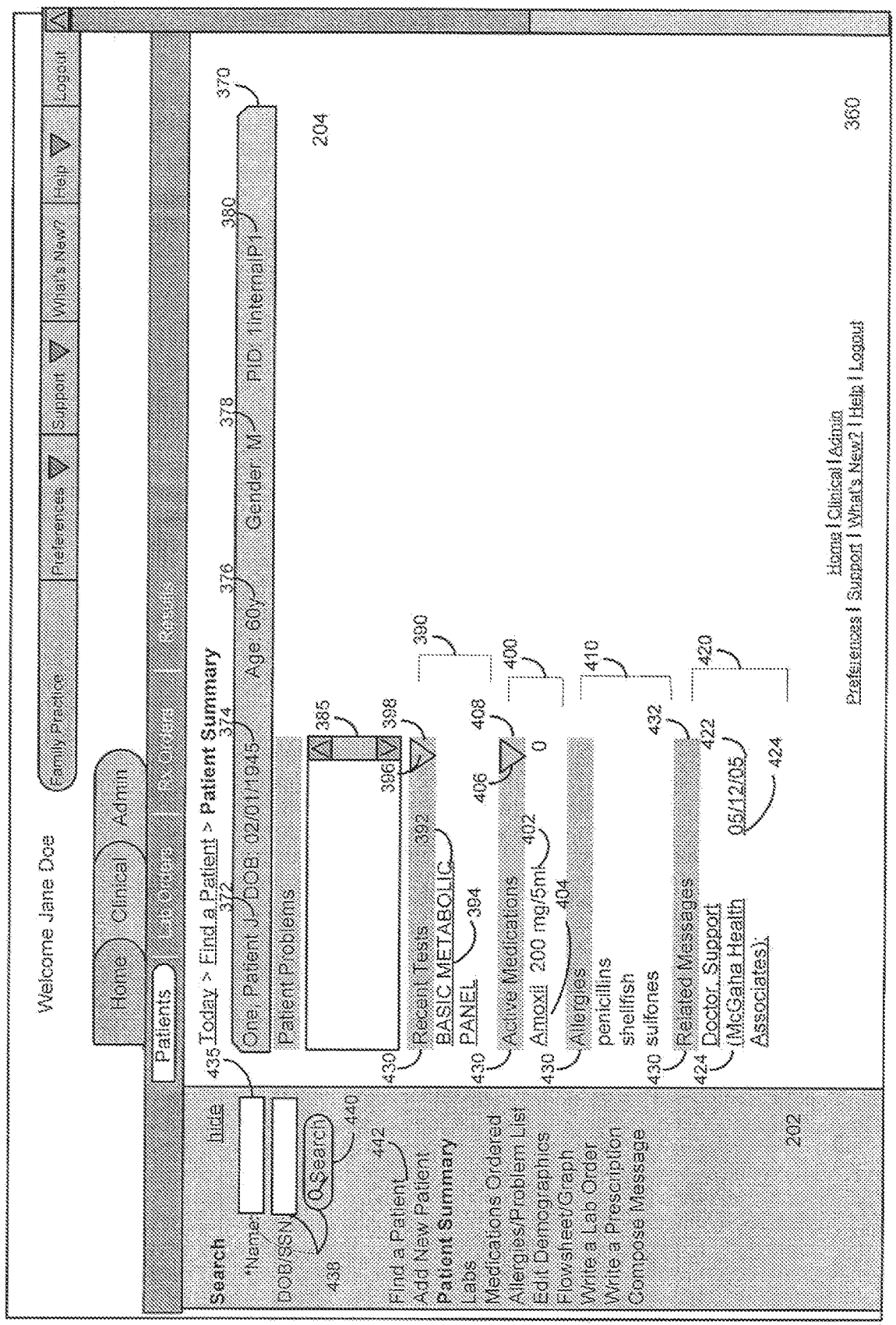
FIG. 4 depicts a user interface display that presents data associated with a patient.

In response to selection of a patient, e.g., via a hyperlink 332, 334, an EHR system may display a summary of data related to that patient, such as the summary screen 360 shown in FIG. 4. In such a system, the summary screen is a "collapsed" or summarized view of the patient's complete chart. The summary screen 360 may initially list only the latest patient data that is available for quick access and review. Viewing a more detailed history for the patient can be done by clicking individual items within each section of the summary screen 360.

The summary appears in the function-sensitive content pane 204 of the summary screen 360. The summary comprises basic information 370 that identifies the patient, including, for example, the patient's name 372, DOB Date of Birth) 374, age 376, gender 378, and PID (Patient ID) 380.

The summary also comprises a display of patient problems and/or conditions, illustrated in FIG. 4 as an editable text area 38 labeled "Patient Problems." This text area 385 may display any problems or other notes that have been recorded for the patient. Some EHR systems allow the user to type notes directly into this control.

An area labeled "Recent Tests" 390 displays one or more lab tests 392 that have been ordered for the patient. The details of a result may be viewed by clicking on the name of the test 394.

Some EHR systems may allow viewing of tests by requisition (order). To support this functionality, the user interface screen illustrated in FIG. 4 displays options (not shown) when the user moves the pointer over the triangle 396 in the title bar 398. For example, in response to a click on the option marked "Requisition" (not shown), tests will be presented, grouped by requisition. Other systems may support other or additional options for viewing lab tests, with appropriate user interface elements to support such options.

Lab tests are discussed in more detail below under the heading "Lab Orders and Results."

An area 400 labeled "Active Medications" displays one or more medications 402 that have been prescribed for the patient (using ePrescribing, described below under that heading) and are still active. Details may be viewed by clicking the name 404 of a medication 402 appearing in this area. The user interface screen illustrated in FIG. 4 allows viewing of all medications prescribed for the patient-including those that are currently inactive or that have been added from other sources-in response to moving the pointer over the triangle 406 in the title bar 408.

An area 410 labeled "Allergies" displays any allergies that have been recorded for the patient.

An area 420 labeled "Related Messages" displays user messages 422 that have been sent that contained a reference to the patient. As displayed in FIG. 4, a user message 422 may contain a hyperlink 424 to more information associated with the message, comprising, for example, the text of the message and some or all data attached to the message. User messages are described in more detail below under the heading "Messaging" below.

Each title bar 430 is a hyperlink or control that gives the user access to further details about the named area. For example, clicking on the "Related Messages" title bar 432 leads to more information about messages. The new information appears in the function-specific content pane 204 of user summary screen 360.

An EHR system may support searching for patients from the user summary screen 360. For example, the search entry area 435 in the function-dependent navigation pane 202 may comprise one or more controls 438 for entering partial or complete search criteria. A search may be executed by selecting the button 440 labeled "Search". An EHR system may provide a means to reach other searching facilities, such as the search screen 290 of FIG. 3, and an example of such means is the hyperlink labeled "Find a Patient" 442 in the function-specific navigation pane shown in FIG. 4.

EHR systems may also provide user interfaces (not pictured) for adding and/or deleting patients and adding, removing, and/or modifying information associated with patients. Such interfaces may use user interface components that are well known in the relevant arts.

ePrescribing

EHR systems may comprise an electronic prescribing function, referred to as ePrescribing. ePrescribing may automate some or all aspects of prescription writing and renewal. In preparing a prescription, ePrescribing may retrieve patient benefit information from an information source such as RxHub® and its participating Pharmacy Benefit Managers (PBMs), which information may then in some embodiments be displayed to the person writing the prescription.

ePrescribing may receive prescription renewals and submit prescriptions electronically or as faxes through an electronic prescribing network such as SureScripts™. Implementations of ePrescribing may support submitting a prescription electronically to the patient's pharmacy of choice, and/or printing the prescription for hand delivery to a pharmacy. Some or all prescriptions written or a patient using ePrescribing may be stored in the patient's medication history, which may be part of the patient's chart maintained by an EHR system. The medication history can be used to store information about inactive medications as well as any additional prescription history retrieved from PBMs.

An embodiment of ePrescribing may provide various different functions that comprise some or all of: displaying information regarding insurance coverage of medications and, depending on the embodiment, possible alternatives; checking for drug-to-drug interactions per prescription, and across the patient's medication history; and drug-to allergy interactions per prescription. ePrescribing may comprise other functions related to medications, prescriptions, insurance, and/or billing besides or in addition to those specifically named.

Figure 5:
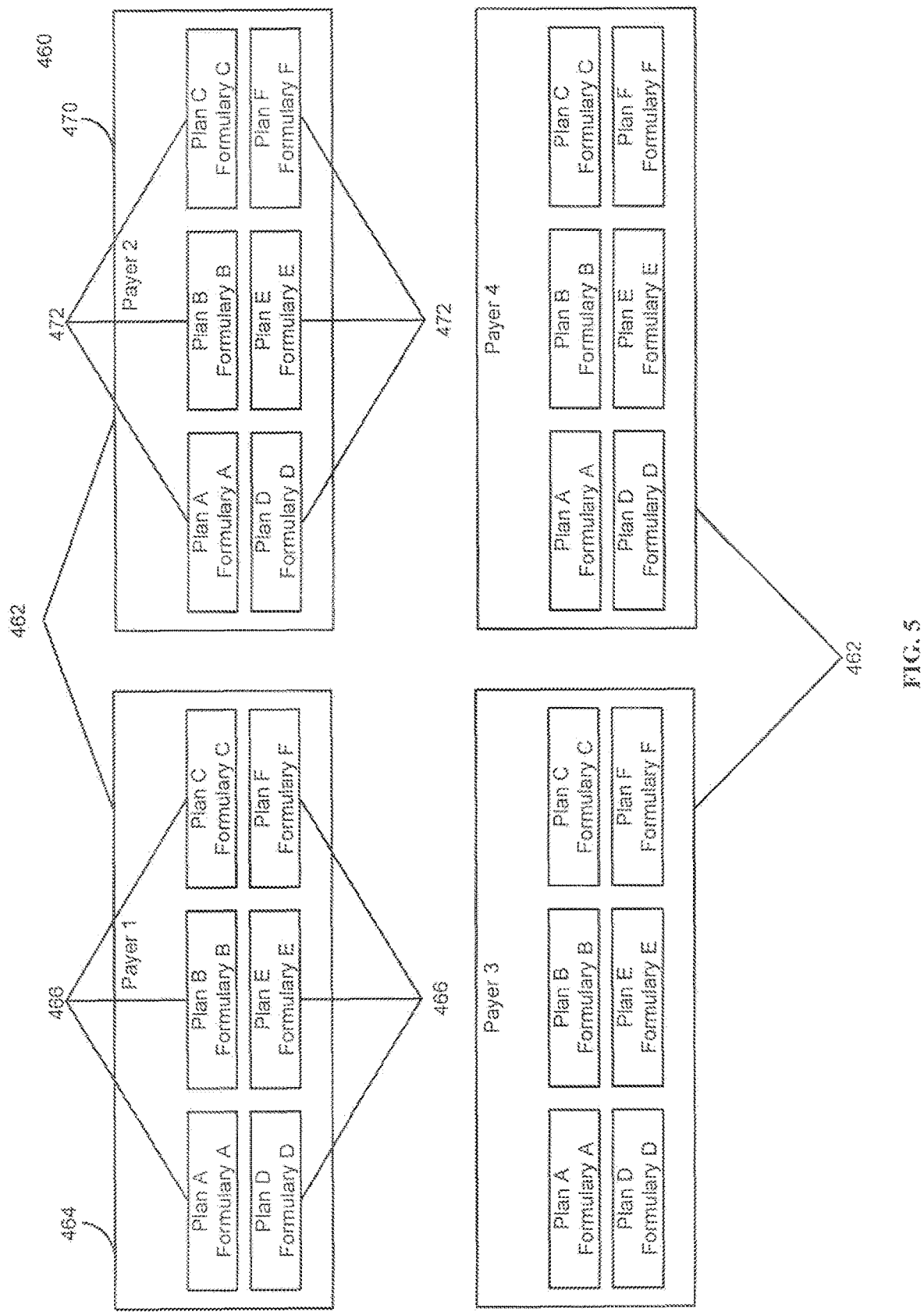
FIG. 5 schematically depicts the relationships between payers, insurance plans, and prescription drug formularies.

An embodiment of ePrescribing may comprise functions related to prescription drug formularies. A formulary is a list of drugs based on a specific payer and a specific payment plan. FIG. 5 illustrates the relationship between payers, plans, and formularies. The figure 460 shows four payers 462. Payer 1 (referenced by 464) offers six different plans 466. If, for example, Payer 1 is an employer, it may offer its employees six different plans 466, each offering different benefits and requiring a different contribution from the employee. Each of these plans 466 is associated with its own distinct formulary.

Similarly, Payer 2 (referenced by 470) offers six different plans and each plan is associated with its own distinct formulary.

Embodiments of ePrescribing may maintain an Active Medications list for patients. When used to create a prescription for a patient, ePrescribing may automatically save a record of each prescribed medication to the patient's Active Medications list, which may be accessible from the patient's summary, displayed in the patient summary screen 360 (FIG. 4). Medications can also be added manually to a patient's Active Medications list by activating previously inactive medications for which ePrescribing has a record and/or by adding them from a list of prescriptions maintained by one or more PBMs.

Embodiments of ePrescribing may support user-specified rules that govern the contents of an Active Medications list. For example, a rule may set the maximum time that a prescription may be considered "active." After that time, a prescription may be removed from the patient's Active Medications list, but may or may not be retained in other records. ePrescribing may also support manual addition to and/or removal from the Active Medications list.

An embodiment of ePrescribing may provide several different ways to display information about a patient's medication history or subsets of it. For example, the Active Medications list and/or the list of all medications on the patient's chart may be displayed and may be sorted according to one or more criteria.

When displaying details of a particular medication, an embodiment of ePrescribing may permit the user to view and/or print a copy of the prescription.

Figure 6:
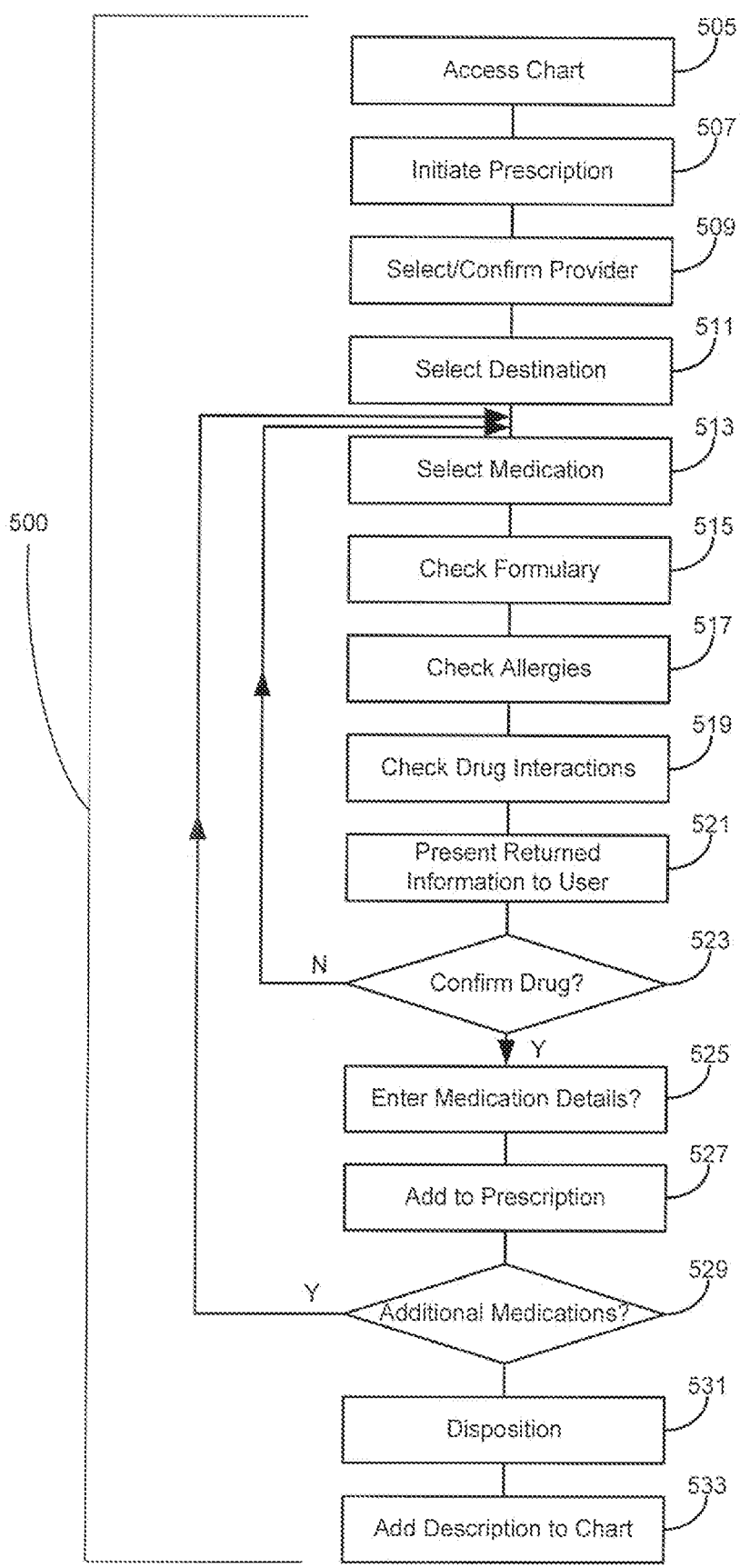
FIG. 6 depicts creation of a new prescription according to an embodiment of an EHR system.

FIG. 6 illustrates how a new prescription may be written 500 in association with an ePrescribing. At block 505, a patient's chart is accessed, possibly as described in connection with FIG. 3, above. Once the patient has been selected, the user may begin 507 creating the prescription.

At block 509, the identity of the health care provider who is writing the prescription is selected or confirmed. In some EHR systems, the user's login information may serve to identify a default provider, who may be the user. Some systems may permit overriding the default choice. Some may limit the choice of provider to one or more providers who have previously been associated with the user.

A destination may be assigned 511 to a prescription. Depending on the embodiment of ePrescribing, possibilities may comprise one or more of, e.g., sample or handwritten prescriptions, prescriptions sent to pharmacies electronically or by fax, and prescriptions sent electronically to mail-order prescription sellers.

Sample prescriptions may represent drugs dispensed directly by the provider, which may be samples provided to the provider by drug makers or distributors. Handwritten prescriptions may, for example, be printed by an embodiment of this application and then manually signed by the provider or manually written in their entirety by the provider. Handwritten prescriptions may be used, for example, where a pharmacy is not equipped to receive prescriptions electronically or by fax, or where applicable law or regulation requires a paper prescription bearing an authorized provider's original signature.

If the prescription is to be sent directly to a pharmacy, block 511 may comprise selection of the recipient pharmacy.

In block 513, a medication is selected for prescribing. Once the medication and the patient are selected, one or more checks may be performed against one or more databases. Depending on the embodiment of ePrescribing, such checks may comprise, for example, one or more of checking the formulary 515 applicable to the patient; checking the drug against the patient's known allergies 517; and checking for interactions 519 between drugs that the patient is known to be taking. Block 521 represents presentation to the user of the results of some or all of these checks.

After reviewing any results of any checks, the provider may confirm 523 the selected drug or to go back choose another medication 513. Once the provider confirms a selected medication, other details of the prescription may be provided 527. Depending on the embodiment of ePrescribing, such details may comprise one or more of, for example, the dosing frequency, the amount of the medication to be dispensed, the length of time that the patient ought to take the drug, the number of refills allowed, and whether a brand-name drug, if prescribed, may be replaced by its generic equivalent, if any.

An embodiment of ePrescribing may support prescriptions that comprise one or more medications. In such embodiments, block 529 represent the choice to add a medication to the prescription that is in progress.

Following selection of desired medications, block 531 represents disposition of the prescription. Depending on the embodiment of ePrescribing and/or the options associated with the prescription, possible dispositions may comprise, for example, printing a prescription for manual signature, transmitting the prescription to a pharmacy electronically or by fax, and/or storing the prescription for possible future action, possibly comprising, among other things, electronic review by a payer. Block 533 represents addition of a prescription to a patient's chart.

Embodiments of ePrescribing may support the association (not pictured) of notes with a prescription and/or some or all of the medications contained in it.

Figure 7:
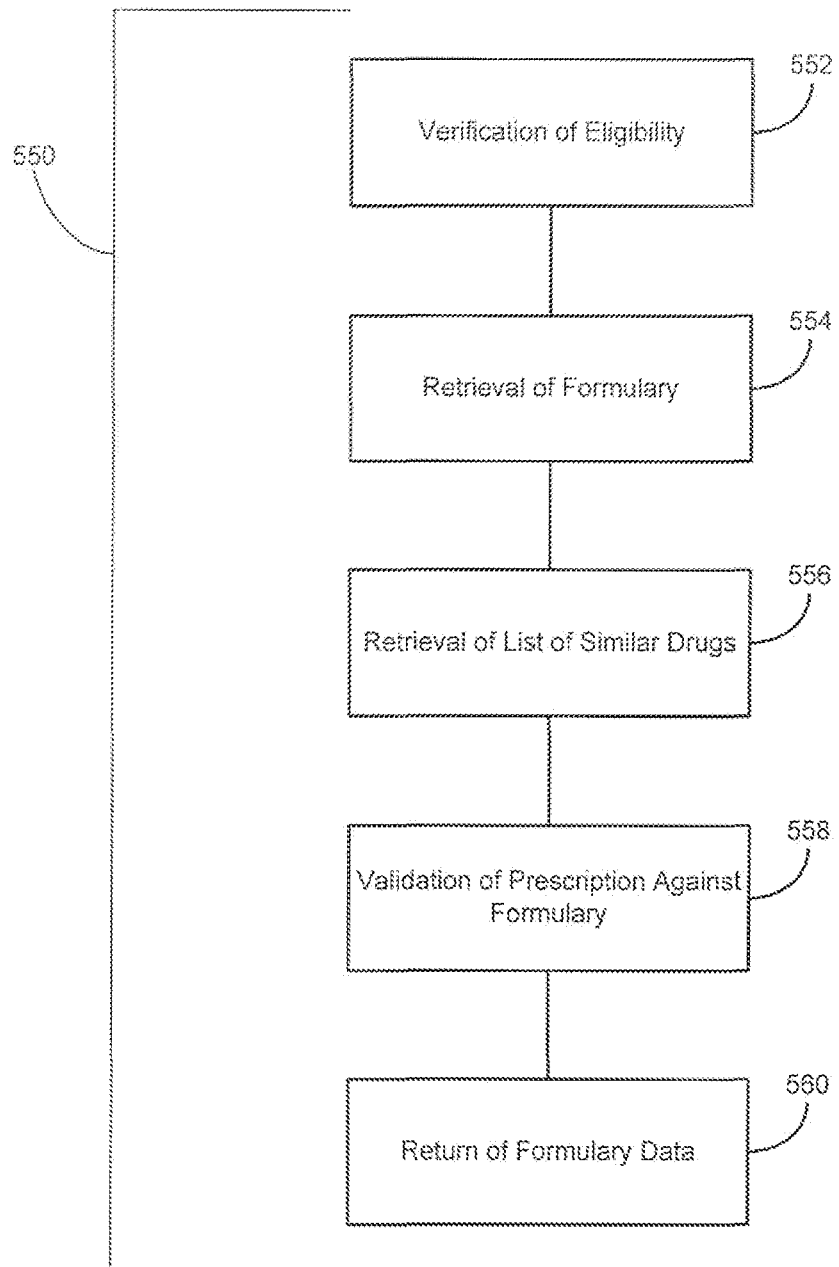
FIG. 7 depicts checking a medication against a particular prescription drug formulary.

FIG. 7 elaborates a possible implementation 550 of checking a formulary. Formularies exist because formulary management may benefit payer organizations. The payers make available the different formulary options to meet both the financial needs of an employer and the benefit needs of employees. But since there are thousands of payers and each payer can have several plans, there are thousands of plans and formularies, all of which may need to be managed.

In block 552, the patient's eligibility for a particular plan is checked against one or more databases. If the patient is eligible, then the appropriate formulary for that plan is retrieved in block 554.

From one or more databases, from the formulary, or both, a list of drugs similar to the prescribed drug is retrieved in block 556. A "similar" drug here is a drug with some or all of the same indications as the prescribed drug or a drug that is prescribed in similar circumstances.

In block 558, the valid of the prescription is checked against the formulary. Finally, in block 560, the results of the other blocks are returned. In some implementations of ePrescribing, the provider will be told that the prescribed drug is or is not on the formulary and will be shown the list of the similar drugs that were identified in block 556. If the information is available to the electronic prescribing system, the provider may also be told what co-payment will be required for the drug.

Other ways (not pictured) exist to check formularies. For example, all relevant formulary data may be obtained at the commencement of an ePrescribing operation. Then, before any information regarding a drug is presented, that drug is checked against the applicable formulary, and the displayed information reflects he formulary status of the drug.

Figure 8:
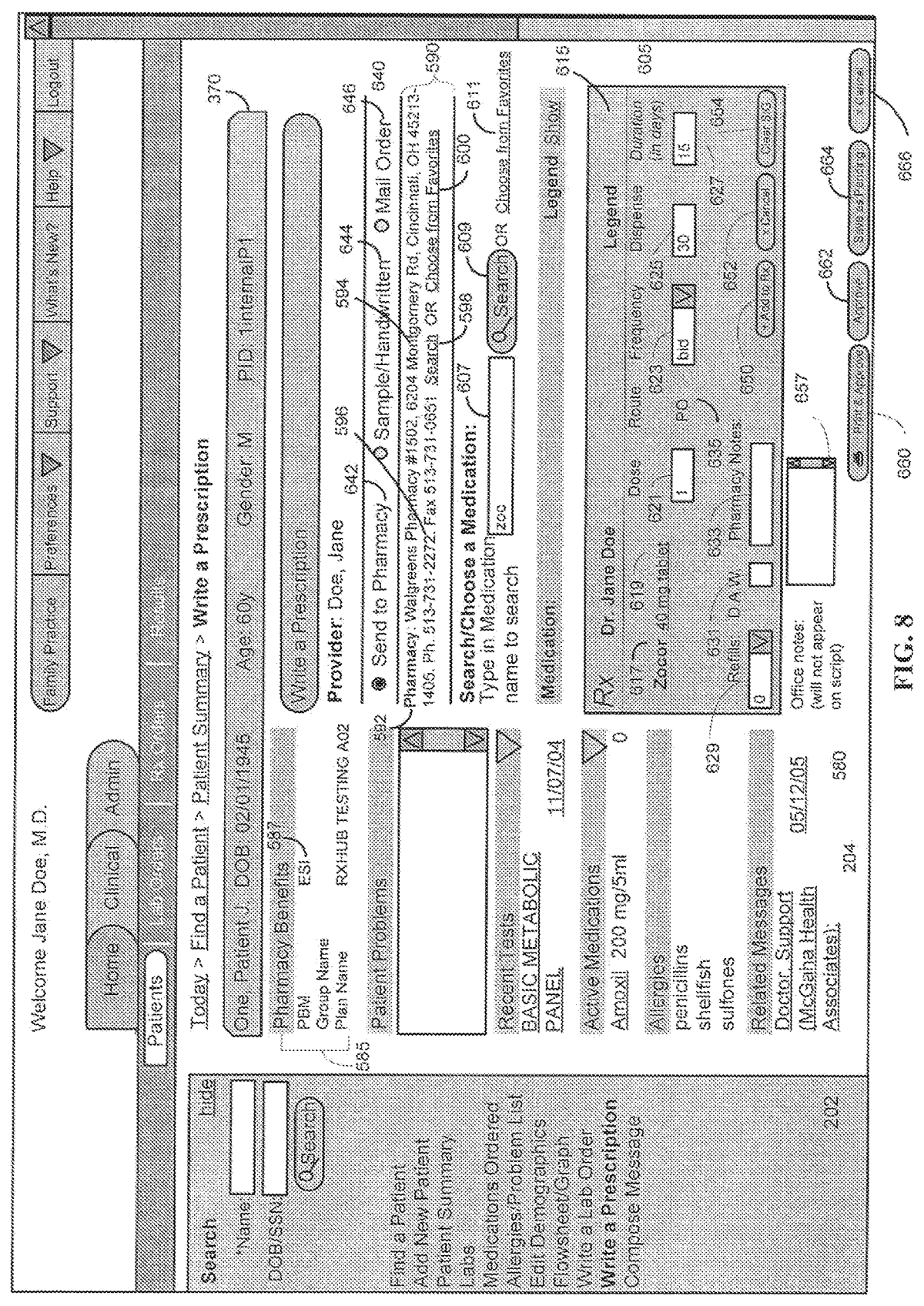

FIG. 8 depicts an example of a prescription writing screen 580 that may he used in association with embodiments of ePrescribing.

As in other example screens, the prescription-writing screen 580 displays basic information 370 that identifies the selected patient. An area 585 holds information about the patient's pharmacy benefits, if known. The information comprises the name of the PBM 587 from which formulary information will be retrieved, if available.

A pharmacy display area 590 holds information about the currently selected pharmacy, which may comprise, for example, the name 592, location 594, and telephone number 596. An embodiment of ePrescribing may set a default pharmacy that may be accepted or modified. A user may select a new pharmacy by following a hyperlink 598, to a screen (not pictured) from which the user may search for a pharmacy, or by following a hyperlink 600 to a display (not pictured) of one or more "favorite" pharmacies, the contents of which depend on the embodiment.

An embodiment of ePrescribing may allow the user to add pharmacies manually (not pictured). Depending on the embodiment, an administrator may allow only a subset of users to add pharmacies manually. Some embodiments may support limiting use of such manually-added pharmacies to one or more subsets of users, and such individual limitations may or may not apply to individual pharmacies and/or one or more classes of pharmacies.

A medication selection area 605 supports searching for a medication to add to the prescription. After a partial or full name of a medication is entered into the text entry control 607, clicking the button labeled "Search" 609 executes a search. From the results of such a search (not pictured), the user may select a medication to prescribe. Embodiments of ePrescribing may also support conducting further searches or other means of selecting a medication once a search has been performed. Also in the medication selection area 605 is a hyperlink 611 that leads to a display (not pictured) of one or more "favorite" medications, the contents of which depend on the embodiment. Selection of a medication may cause display (not pictured) of one or more forms and/or dosages in which that medication may be dispensed.

Any display of information related to a medication may comprise information regarding formulary status of that medication. Many ways of conveying such information are well known, and may comprise, e.g., arranging names of medications in a display; providing textual labels; visually associating one or more icons with the displayed medication; and/or varying the typeface, size, style, color and/or other attributes of the text used; among other indications.

In addition to or instead of the preceding, any display of information related to a medication may comprise information regarding interactions between that medication and a patient's allergies and/or other medications that a patient is known to be taking. Display of such information may take varying forms as above.

Display of information related to a medication may comprise display of information regarding other medications, comprising, for example, generic equivalents to a medication and/or possible alternatives to a medication.

The Rx Box 615 displays a selected medication 617 and its dosage and form 619. It contains controls that support entry or modification of information associated with a prescription, such as the dose 621, frequency 623, amount to be dispensed 625, duration of the prescription 627, number of refills permitted 629, authorization to dispense a generic equivalent instead of a brand-name drug 631, and notes 633, if any, for the pharmacy. A code 635 indicates the preferred route for administration of the medication. Some embodiments of ePrescribing may cause additional and/or different controls to be displayed.

As illustrated, the dose 619 is a hyperlink to a screen (not pictured) allowing selection of a different dose, if available.

A destination area indicates where a complete prescription is to be sent. As depicted, the options presented comprise "Send to Pharmacy" 642, "Sample/Handwritten" 644, and "Mail Order" 646. Options may be disabled depending on circumstances. For example, when used to create a prescription for a controlled substance that may be dispensed only upon a manually signed prescription, an embodiment of ePrescribing may disable the "Send to Pharmacy" 642, and "Mail Order" 646 options.

Once a medication has been selected and appropriate parameters set, a button 650 allows addition of the medication to the current prescription. Another button 652 causes removal of the medication from the current prescription. A button 654 is provided to clear the currently-entered values.

Embodiments of ePrescribing may provide functionality and interfaces (not pictured) supporting renewal of previous prescriptions and/or for using previous prescriptions as models or templates for new ones.

The screen 580 also displays a control 657 that supports entry of office notes that are associated with the prescription as a whole, but may or may not be associated with any individual medication contained in the prescription. Depending on the embodiment of ePrescribing, such office notes may or may not appear on a prescription itself.

The screen 580 displays controls 660, 662, 664, 666 associated with the disposition of prescriptions. Depending on the embodiment of ePrescribing, a button 660 causes a prescription to be printed, an image of a prescription to be displayed that may itself be printed, or both. A button 662 indicates approval of the prescription as currently displayed. Selecting this button 662 may cause the prescription to be sent to the selected pharmacy, to be held pending approval by a PBM, and/or other possible dispositions. A button 664 causes the prescription to be saved as a pending prescription, and, in some embodiments, the prescription may be held pending approval by a PBM. Finally, a button 666 may cancel a prescription.

Information about pending and sent prescriptions may appear on screen 200 (FIG. 2) in the Action Items area 264 (FIG. 2). Such information may comprise, for example, the number of pending prescriptions and/or the number of electronic or faxed prescriptions that failed to reach their destinations. In some embodiments of ePrescribing, a hyperlink such as the hyperlink 280 (FIG. 2) illustrated may lead to a display (not pictured) adapted to resolution of one or more such action items.

The preceding description of ePrescribing is meant to be illustrative, not limiting. Embodiments of ePrescribing may provide functionality and user interfaces different from and/or in addition to those described. To may be provided to search, retrieve, display, modify, and/or otherwise manipulate data associated with prescriptions and/or associated medications, whether singly, in groups, or both.

Lab Orders and Results

EHR systems may support entry of orders for lab services and/or display of results of lab tests. More particularly, a user interface may support specification of one or more lab tests to be performed and, depending on the system, may automatically submit a request for such tests to a provider of lab services (a "lab"). Automatic submission of a request may take place electronically, by fax, and/or by other means. Labs may provide test results for storage, processing, and/or display. An EHR system may insert some or all lab orders and/or results into the involved patient's charts.

EHR systems may support entry of orders for lab services and/or display of results of lab tests.

Figure 9:
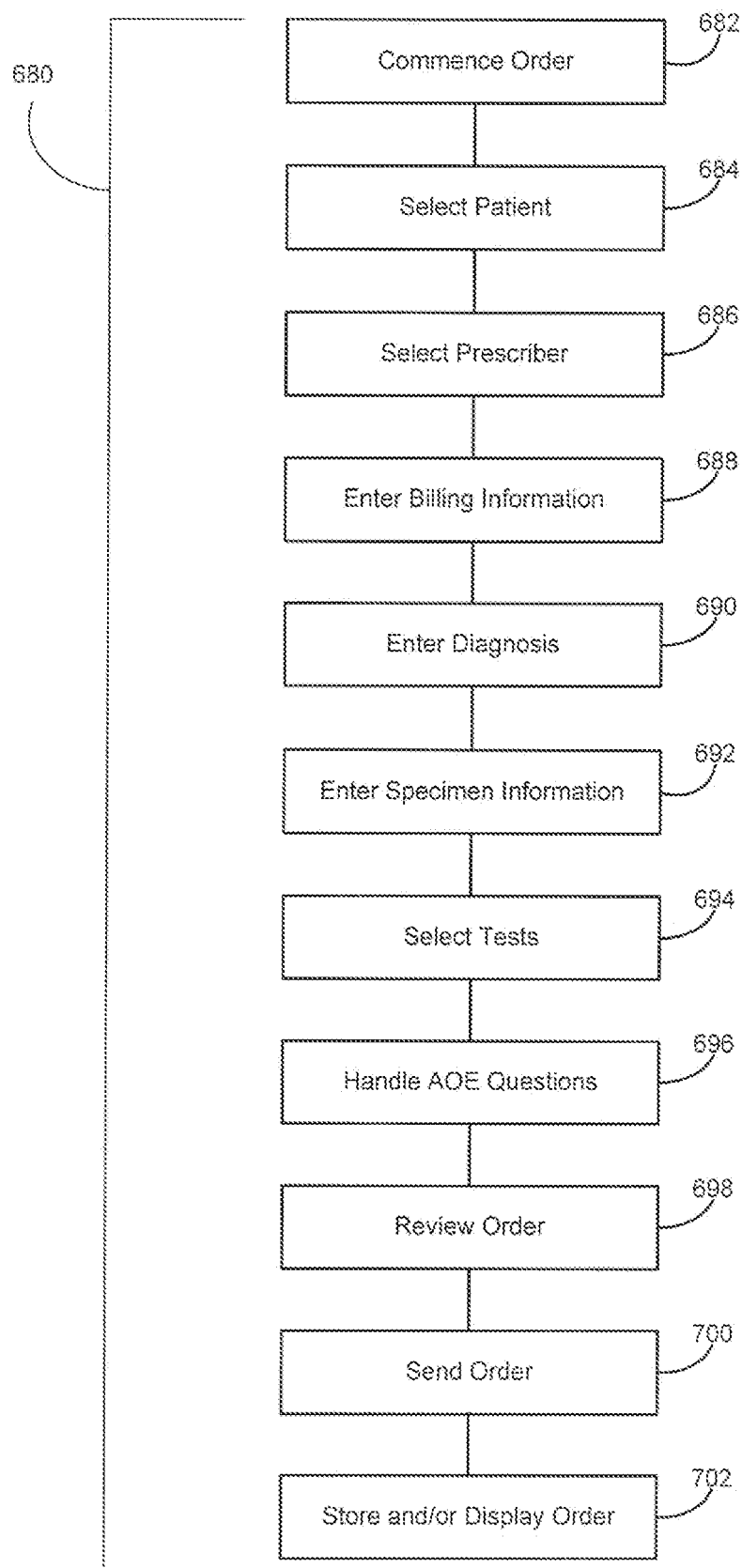
FIG. 9 depicts ordering laboratory services according to an embodiment of an EHR system.

FIG. 9 depicts how a new order (also called a "requisition") may be created 680. In block 682, a user interface adapted to creation of an order is displayed. In block 684, a patient is associated with this order. If order creation 680 has been initiated from a screen such as patient summary screen 200 (FIG. 2), a patient may already be associated with this order. An EHR system may provide functionality as already described herein to select a patient to associate with this order.

Block 686 represents selection of the health care provider who is ordering the test. EHR systems may support use of one or more unique codes and/or identifiers in connection with selection of a provider. For example, an EHR system may restrict the ability to order lab tests to physicians, and such a system may support use of the ordering physician's Medicare Unique Physician identification Number ("UPIN") to uniquely identify that physician.

An EHR system may support entry 688 of billing information for the associated patient and/or verification of such information already provided. Such information may comprise, for example, the name of the person who bears financial responsibility for the patient and/or information regarding the patient's insurance or other payment arrangements. An EHR system may use this information in conjunction with one or more facilities for automating payment, billing, and/or collection.

In block 690, one or more diagnoses associated with the patient may be entered. Diagnoses may be represented by one or more codes, e.g., codes from the standard International Classification of Disease (ICD). An EHR system may accept locally-defined codes in addition to or instead of standard codes. Similarly, an EHR system may accept textual specifications of diagnoses in addition to or instead of codes of any sort.

One or more specimens may be subjects of lab tests. Block 692 represents entry of information regarding a specimen associated with a test order. Such information may comprise, for example, the date and time the specimen was collected, the volume of the specimen, and/or whether the patient fasted. An EHR system may vary the information collected depending on which test is selected and/or may refuse to accept an order that omits some or all information.

In block 694, depending on the system, one or more lab tests may be selected. Also depending on the system, a user may select from tests offered by one lab or from a plurality of labs.

An EHR system may provide access to one or more tests that require additional information before a lab can perform the tests. In block 696, such Ask at Order Entry ("AOE") information can be obtained and added to the order information.

An EHR system may use entered patient, payment, diagnosis, order, and/or ACE information to verify (not pictured) that a test order will be covered by the patient's payment plan. Such a system may indicate coverage status visually.

Block 698 depicts review of entered order information. In some EHR systems, creation 680 of a lab order may be interrupted (not pictured) at this point, with the order information stored for future use, in such a system, such stored information may be retrieved and the order completed. Once the information is believed correct, the order may be sent in block 700 to, depending on the embodiment, one or more labs for processing. In block 702, a sent order may be stored, possibly in association with the patient's chart.

Sending an order as depicted in block 700 may comprise sending the order to a lab electronically, by fax, and/or other means, depending on the EHR system and/or its configuration.

Following creation 680 of a lab order as depicted in FIG. 9, an EHR system may arrange automatically for retrieval (not pictured) of the physical specimen or specimens associated with one or more ordered tests. Such arrangements may comprise, for example, adding the location of the health care provider's office to the route of a courier who picks up such specimens. In some EHR systems, an order may request that a technician be dispatched to the patient's location (e.g., home or office) to obtain a sample. Another possible arrangement may involve automatic generation of shipping orders and documents for a common carrier such as UPS® or FedEx®. It will be appreciated that many other such arrangements are possible.

An EHR system may support variations of lab order creation 680 in addition to or instead of creation 680 as depicted. For example, information entered as described may serve to create a standing lab order, which may be repeated as specified by the user. A previously-entered order may serve as a template for creation of a new order. Many other variations are possible and may be supported by an EHR system.

Test results may be provided electronically to an EHR system. An EHR system may accept result in other forms, e.g., results printed on paper may be accepted via optical scanning or manual data entry. Other ways to provide and accept test results are apparent. An EHR system may accept test results regardless of whether a test was electronically ordered.

An EHR system may receive one or more test results that lack information sufficient to match the results with a requisition or a patient. A system may thus provide one or more facilities for matching such orders with the corresponding records.

Figure 10:
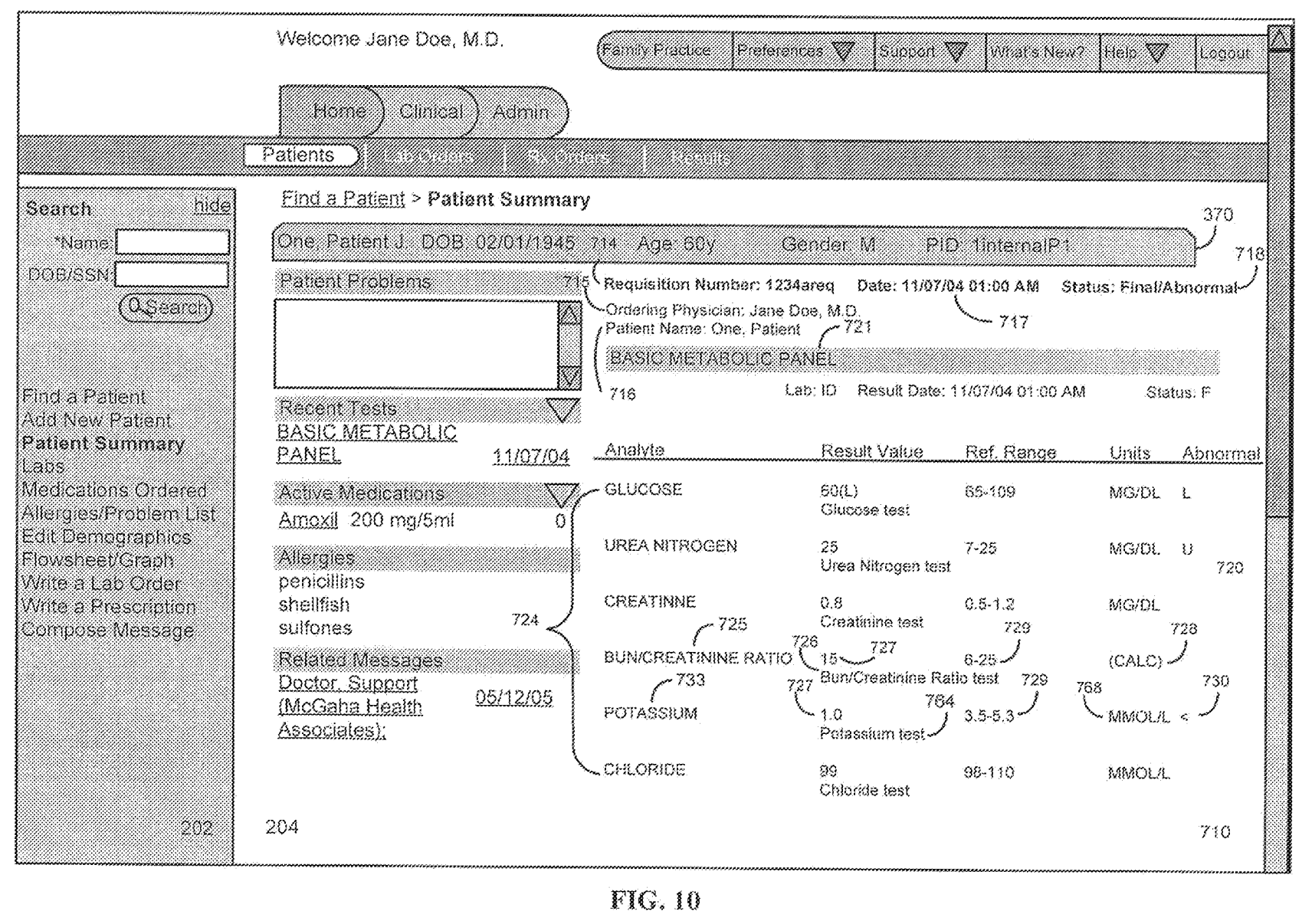

FIG. 10 depicts the test result screen 710 that may appear in an EHR system. An EHR system may provide one or more ways to reach test results, and one way that the depicted screen 710 may be reached is from the patient summary screen 360 (FIG. 4). The test result screen 710 comprises basic information 370 that may identify the patient associated with a test. The test result screen 710 may comprise other information about the test results and the associated requisition, e.g., a requisition number 714, the prescriber's name 715, the patient's name 716, the date and/or time when the tested sample was obtained 715, and/or a summary 717 of the test results, among other things.

Test details 720 may be presented. A title bar 721 indicates the name 722 of the test and/or panel of tests. Below the title are the results 724 of one or more tests.

As illustrated in the test result screen 710, a test result 724 comprises the name 725 of a substance or property (either may be called an "analyte") for which a test was performed. The result 724 may also comprise a short description 726 of the test or analyte; a number representing the value 727 of the analyte; and/or the units 728 of the measurement. For reference, a range 729 of typical values for the analyte may be provided, as well as one or more visual indications 730 that a measured value is abnormal.

For example, the test result screen 710 illustrates the results of a panel of tests called a "Basic Metabolic Panel." One test in the panel is a test for potassium 733. The reference range 729 for potassium is between 3.5-5.3 millimoles per liter, but the test measured only 1.0 millimoles per liter 727. A "<" character 730 thus appears to the right of this abnormal result, indicating that measurement was below a range that may be considered normal. A user interface screen may comprise other indicia of abnormal test results, e.g., symbolic icons and/or text coloring.

Test results over time may be presented. For example, graphs and/or charts (not pictured) may depict the values of one or more tests over time. A report may present the same information textually. Other ways of presenting test results will be apparent, and an EHR system may comprise any or all such presentations.

An EHR system may comprise search, retrieval, and/or report generation facilities (not pictured). Such facilities may, depending on the system, comprise manipulation of one or more test results for one or more patients, individually or collectively. For example, an EHR system may allow a user to search for results of all glucose tests given in the past month to male patients between the ages of 45 and 59, in which the test detected an abnormal level of glucose. Such facilities may serve, for example, to identify clusters of abnormal test results, which may in some circumstances signal a spreading health problem. An EHR system may comprise tools for creating graphical and/or textual reports of such searches.

Flowsheets

An EHR system according to embodiments of the invention may comprise facilities for presenting lab test results and data related to medication usage for a patient across a specified period of time, in a particular form that is referred to herein as a "Flowsheet." Depending on the embodiment of the invention, data may be stored in an EHR system as a result of the lab ordering and results and/or ePrescribing functions described above. In addition to or instead of the foregoing, data in an embodiment of the invention may be entered and stored manually. Such an embodiment may comprise various ways to specify the data included in the Flowsheet and to navigate through the data shown to view the specific data desired.

Figure 11:
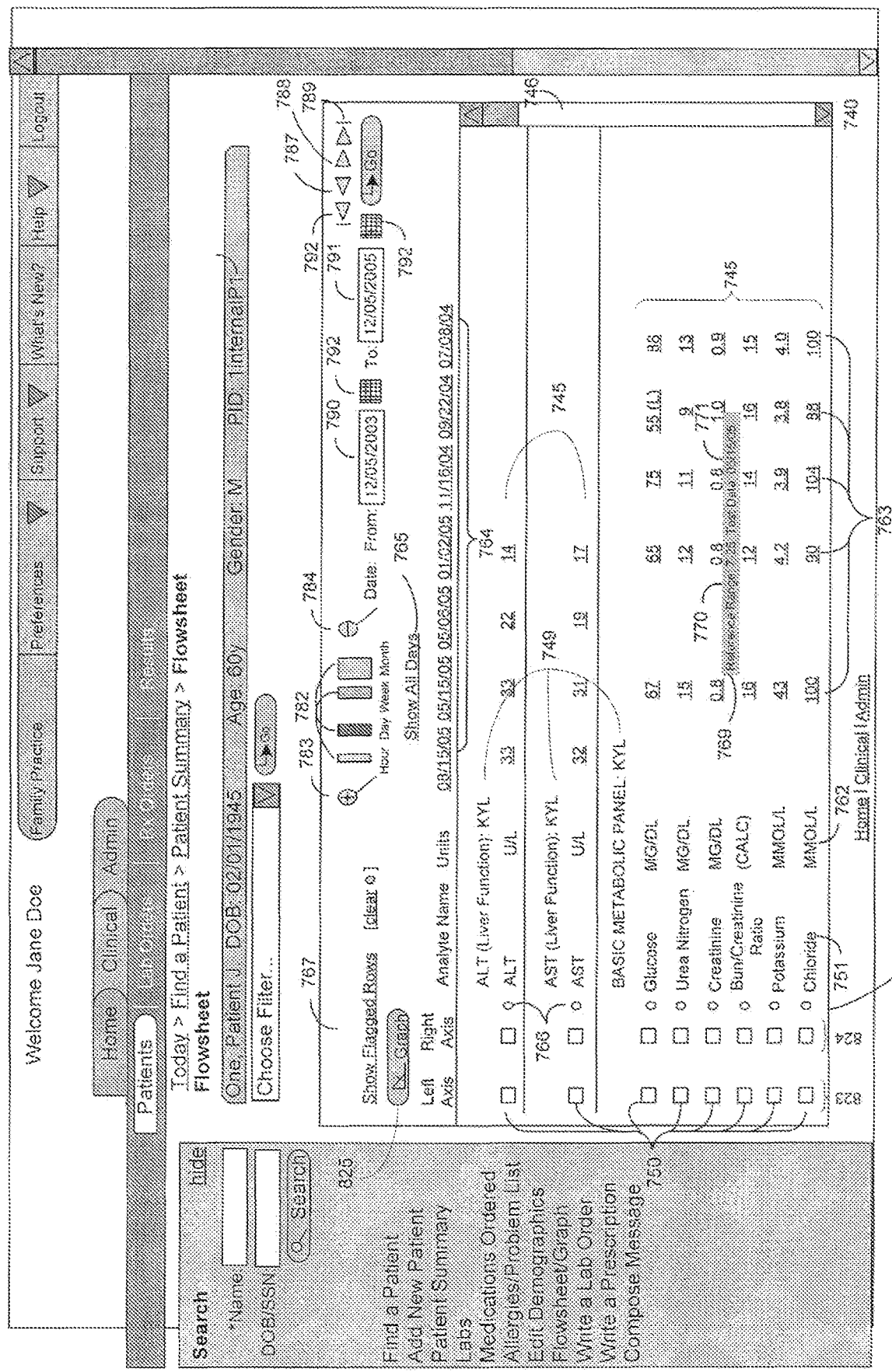
FIG. 11 depicts a user interface display that presents a Flowsheet according to an embodiment of the invention.

FIG. 11 depicts a user interlace display 740 that comprises a Flowsheet 741. The Flowsheet displays at least one test result 745 and/or at least one prescription (not pictured). (In connection with the depicted embodiment, the term "clinical event" may refer interchangeably to a test result or a prescription. Other embodiments may implicitly or explicitly rely on different meanings of the term.) In the depicted embodiment of the invention, test results 745 and prescriptions (not pictured) appear in separate display regions, but another embodiment (not pictured) may present all clinical events in a single region.

If a Flowsheet 741 contains more clinical events 745 than will fit in the display window, a scroll bar 746 may be used to bring additional clinical events into view.

For a test result 745, the displayed information may include, e.g., a caption 749 and results for one or more analytes 750. A result for an analyte 750 may include, e.g., the name (or identifier) 751 of the analyte, the units 762 used to measure the result, and the measured values 763 of the analyte on one or more dates 764. In the depicted embodiment of the invention, the dates 764 also serve as column headings.

In the depicted embodiment of the invention, the Flowsheet by default displays only those dates (hour, day, week, or year) for which result values have been received; all dates that do not contain values are initially hidden. The hyperlink 765 labeled "Show All Days" causes the Flowsheet to show all days, regardless of whether or not they contain data. When all dates are shown, the caption of the hyperlink 765 changes to "Show Activity Days," and, when selected, causes the display to return to the default (in which empty dates are hidden). This text of the hyperlink 765 changes ("Hours," "Days," "Weeks," or "Months") to indicate the zoom level (discussed below) that is currently displayed.

In an embodiment of the invention, the display may be limited to only selected analytes or medications. For example, as depicted in FIG. 11, each analyte and medication is associated with its own circular icon 766, indicating whether the item has been selected. When selected by the user, the icon 766 appears darker (not pictured). One the desired items have been selected, the display may be limited by selection of the hyperlink 767 captioned "Show Flagged Rows." When the display is so limited, the caption of the hyperlink 767 may change to read "Show All Rows" or something similar, and selection of the hyperlink 767 returns the Flowsheet 741 to display of all rows.

In an embodiment of the invention, additional information about an analyte appears in a pop-up region 769 when the pointer (not pictured) pauses over an analyte 750. For example, in the embodiment depicted in FIG. 11, the pop-up region 769 comprises a reference range 770, which may be a range of typically observed values for the analyte. The pop-up region 769 also displays the date 771 on which the test was performed.

In an embodiment of the invention, further information about a particular result for a particular analyte may be obtained by clicking on a value 763. Such an embodiment may, in response, open a new window presenting details for the result. FIG. 12 depicts an example of such a details window 773.

For a lab test result, the details window 773 may present, for example, the measured value 763 of the analyte, the reference range 770, the office 774 at which the test was performed, the order number 775, the name 776 of the physician who ordered the test, the time and date 777 at which the test sample (e.g., blood, urine, saliva, etc.) was obtained, an accession number 778 that uniquely identifies the test sample, the identity of the laboratory 779 that performed the test, and any comments 780 that may be present in the test record. For a prescription, the details window (not pictured) may present, for example, the drug name, quantity, frequency, dose amount, dose form description, strength, and date prescribed. An embodiment of the invention may present other information instead of, or in addition to, the depicted information.

According to an embodiment of the invention, a Flowsheet 741, as depicted in FIG. 11, comprises several user interface controls for navigating within a Flowsheet and/or otherwise controlling the content and/or appearance of the Flowsheet 741.

One such control, comprised by an embodiment of the invention, allows selection of the time scale for presentation of data. In the Flowsheet 741 depicted in FIG. 11, the scale may be "zoomed" in or out, to present the data by hour, day, week, or month. The selector bars 782 permit direct selection of the desired time scale. Selection of the "plus" 783 or "minus" 784 magnifier icons causes the scale to zoom in or out, respectively.

In the depicted embodiment of the invention, if two or more values exist for the same date, the Flowsheet indicates the average of the values. Other treatments are possible, e.g., using the first (or last) measurement for the date.

A patient's chart may include results for more dates than will fit within the width of a single page of the display 740. In an embodiment of the invention, the user interface display may comprise controls (arrows, in the depicted embodiment) that, when selected, lead to display of the first page 786, previous page 787, next page 788, or last page 789, respectively. In the depicted embodiment, the Flowsheet initially contains the most recent results available for the patient, but other embodiments may have other default settings.

According to an embodiment of the invention, the Flowsheet 741 may comprise date range fields, whereby the beginning 790 and end 791 of a range of dates to be displayed in the Flowsheet 741. Other controls, e.g., calendar controls (not pictured) accessed through hyperlinked icons 792, may also support entry of such a range of dates.

Figure 13:
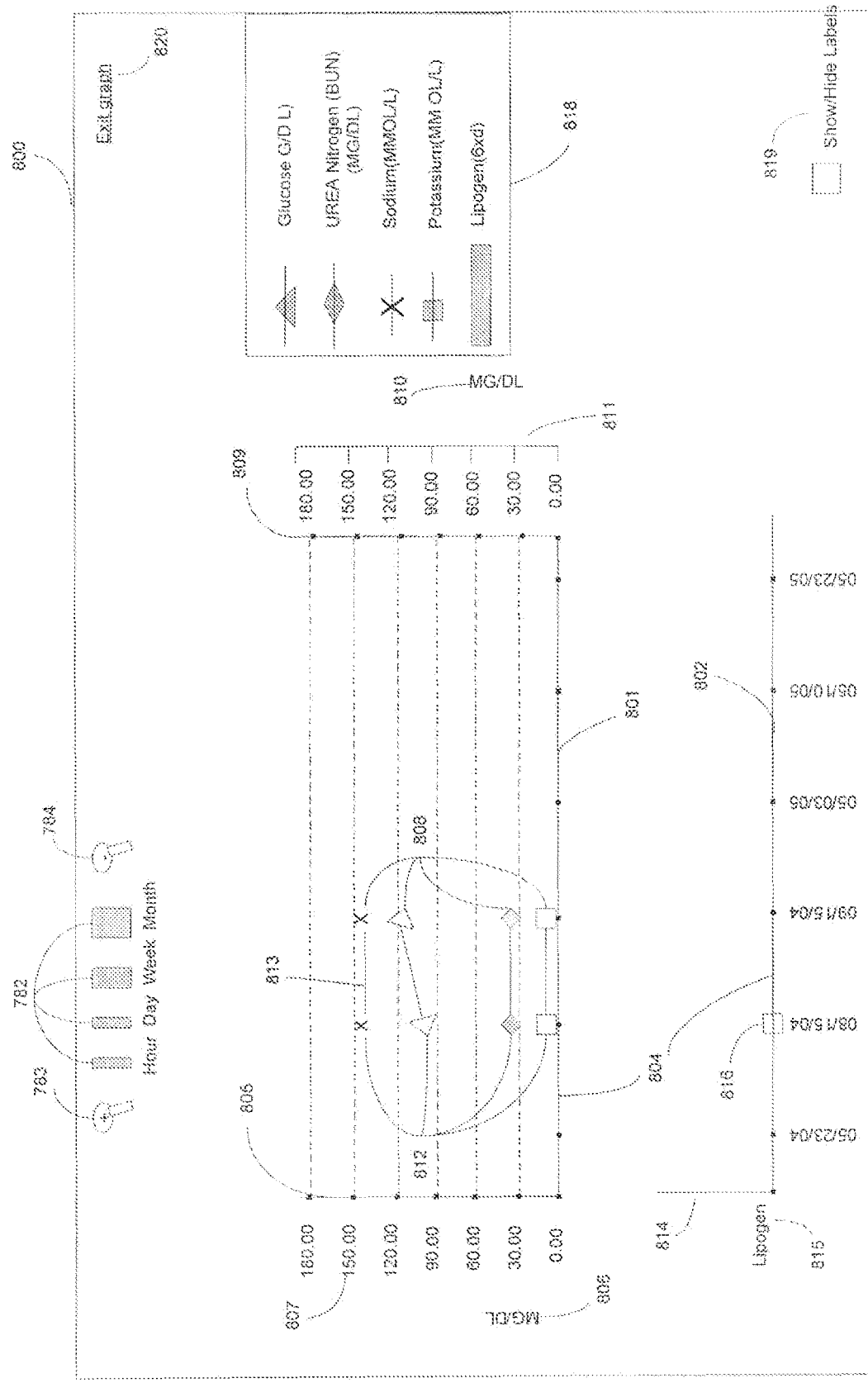
FIG. 13 depicts a user interface display that presents graphs of test results and medications according to an embodiment of the invention.

In an embodiment of the invention, one or more displayed analytes and/or medications may be selected and then presented visually by generating a graph. FIG. 13 depicts a single user interface display 800 presenting two graphs 801, 802, according to an embodiment of the invention. According to the embodiment, if both analytes and medications are selected at the same time, each is presented in a separate graph.

An analyte graph 801 comprises a horizontal axis 804 that indicates time, a left vertical axis 805 that indicates the unit of measurement 806 and scale 807 for values one or more of the presented analytes 808. An analyte graph 801 may comprise a right vertical axis 809 that indicates a second unit of measurement 810 and a second scale 811 for values of one or more additional presented analytes 808.

A data point, which in the analyte graph 801 represents the value of an analyte on the indicated date, appears as a symbol 812, e.g., a triangle, a diamond, or an "X" in the depicted embodiment. Line segments 813 connect sequential data points for the same analyte.

As with an analyte graph 801, a medication graph 802 comprises a horizontal axis 804 that indicates time. A medication graph 802 also comprises a vertical axis 814 that indicates the name 815 of each graphed medication. A bar 816 represents a prescription for a particular drug on the indicated date, which, on the medication graph 802, constitutes a data point.

Besides or in addition to the depicted symbols, different colors may also indicate the analyte or medication associated with a data point. To indicate the meaning of the symbols and/or colors, a legend 818 may be provided, as depicted in FIG. 13, to the right of the graph or graphs 801, 802 in FIG. 13. The Show/Hide Labels check box 819 is a toggle that controls whether the display includes the numeric values (not pictured) associated with each data point on the graph.

In an embodiment of the invention, each data point represented in the analyte graph 801 comprises a value that is recorded in using either the unit of measurement 806, indicated by the left vertical axis 805, or the second unit of measurement 810, indicated by the right vertical axis 809. The connections between the underlying data points and their units of measurements may be depicted in the analyte graph 801 as associations between the symbols 812 and the appropriate vertical axes 805, 809. As depicted in FIG. 13, these associations are indicated in the legend 818 by the units of measurement placed next to the symbols. Embodiments of the invention may indicate these associations in different and/or additional ways, e.g., by the colors of the vertical axes 805, 809 and/or the symbols 812, the placement of symbols 812 and/or other markers relative to one or both of the vertical axes 805, 809, etc.

In an embodiment of the invention, additional details about a data point pop up (not pictured), if the pointer is held over that data point.

As described in connection with the Flowsheet 741, zooming controls 782, 783, 784 may be provided for changing the resolution at which data is displayed in the graphs 801, 802. In the depicted embodiment, the window containing the graph or graphs may be closed using the hyperlink 820 labeled "Exit graph."

In an embodiment of the invention, the analytes and/or medications included in a graph may be selected from a Flowsheet 741 as depicted in FIG. 11. Returning to FIG. 11, Flowsheet 741 comprises a first column of check boxes 823, captioned "left axis," and a second column of check boxes 824, captioned "right axis." In this embodiment, an analyte 808 may be selected for inclusion in the analyte graph 801 (FIG. 13) by selection of one of the checkboxes 823, 824 in the analytes row.

In this embodiment of the invention, analytes 750 that use up to two different units of measure may be selected for display on the same graph 801 (FIG. 13). In such case, the first unit of measure appears on the left vertical axis 805 (FIG. 13), and the second unit of measure appears on the right vertical axis 809 (FIG. 13). The collection dates for the selected analytes appear along the horizontal axis 804 (FIG. 13).

In the depicted embodiment of the invention, selection of the checkbox next to a first analyte 750 in the Left Axis column 823 (FIG. 13) will disable all other checkboxes in this column next to other analytes 750 that use different units of measure. It will also disable all checkboxes in the Right Axis column 824 next to analytes 750 that use the same units of measure as the first analyte 808. The converse occurs in response to selection of the checkbox next to a second analyte 750 in the Right Axis column 824. This process reflects the limitation of an analyte graph 802 in the depicted embodiment to vertical axes 805, 809 (FIG. 13) reflecting only two units of measure 806, 810 (FIG. 13). An embodiment that presents more vertical axes may omit or alter this process accordingly.

In an embodiment of the invention, a medication graph 802 (FIG. 13) includes only one vertical axis 814 (FIG. 13), on the left side. In such an embodiment, the Flowsheet row for a medication will include only a single checkbox in the Left Axis column 823. The prescription dates for the selected medications appear along the horizontal axis 804 (FIG. 13).

Once all of the desired analytes and/or medications have been selected, the control labeled "Graph" 825 may be used to display a new window comprising a display 800 (FIG. 13) of one or two graphs.

Embodiments of the invention may provide one or more facilities by which filters may be used to limit the data appearing in a Flowsheet. A filter may include or exclude one or more chart items based on a characteristic of the chart items. For example, a filter may include only laboratory reports, or only medications. Another filter may include only reports containing abnormal laboratory results. The characteristics that may be the basis of a filter depend on the embodiment of the invention. Some embodiments may permit application of more than one filter at a time.

Embodiments of the invention may provide for printing hard copies of Flowsheets, graphs, or both.

An embodiment of the invention may support storage, retrieval, editing, and/or sharing of flowsheets. For example, a user interface displaying a flowsheet or a graph may comprise a control (not pictured) that, when selected, causes the Flowsheet's and/or graph parameters to be stored to a database. (Depending on the embodiment of the invention, the stored parameters may comprise, e.g., the names of the analyte(s) and/or medication(s), the date range and/or scale, the identity of the patient associated with the data, any applicable filters, etc.) This storage may, e.g., be in association with the patient's chart (not pictured), and, in such an implementation, retrieval of a stored flowsheet may be through a user interface comprising a display of data from that chart.

An embodiment of the invention may support sharing of stored flowsheets. For example, a reference that uniquely identifies a flowsheet may be passed from one user to another in an electronic message, as described snore fully below under the heading "User Messaging".

User Messaging

An EHR system may comprise an electronic messaging facility. In such a system, users can communicate with other users whether they reside in the same organization or care site, reside in a separate physical office location, or are members of a separate organization. An EHR system may make it possible to refer, within the user message, to specific clinical acts for a patient, including, for example, lab reports, medications, and/or allergies. This function may be desirable for purposes related to patient care, including, for example: patient referrals; answering of patient questions; and providing care instructions to other clinicians.

Figure 14:
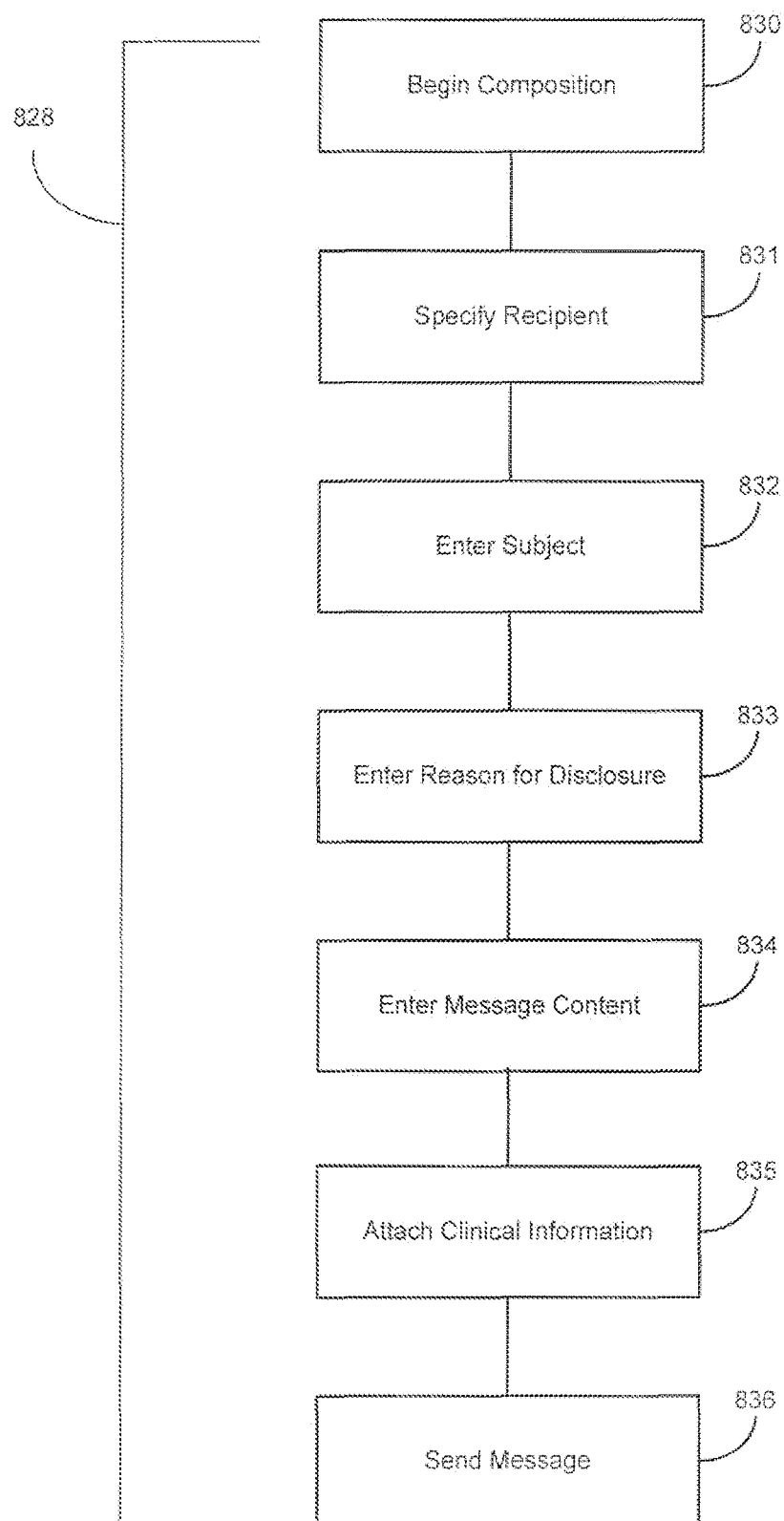
FIG. 14 depicts composing and sending an electronic message according to an embodiment of an EHR system.

FIG. 14 depicts composing and sending 828 a message in an EHR system. An EHR system may support one or more means to begin 830 composing a message. For example, in the patient summary screen 360 (FIG. 4), the function-dependent navigation pane 202 (FIG. 4) may contain a hyperlink 446 (FIG. 4) to a user interface that supports composing a message.

In block 831, the user may specify one or more message recipient(s). EHR systems may differ on how recipients are specified. For example, an EHR system may provide a control (not pictured) in which a name or address of a recipient may be entered. An EHR system may provide the names of one or more known users, from whom one or more recipients maybe selected. These and other ways of selecting recipients are well known in connection with electronic messaging, and EHR systems may support one or more such ways.

Other information may be entered; for example, an EHR system may support entry of a message subject 832, a reason for disclosure of patient information 833, and/or the content of the message 834. An EHR system may, for example, support entry of a reason for disclosure of information to track the distribution of health information that is required by law to be kept confidential.

If desired, clinical information from a client's chart may be attached 835 to the user message. The user message may then be sent 836.

Figure 15:
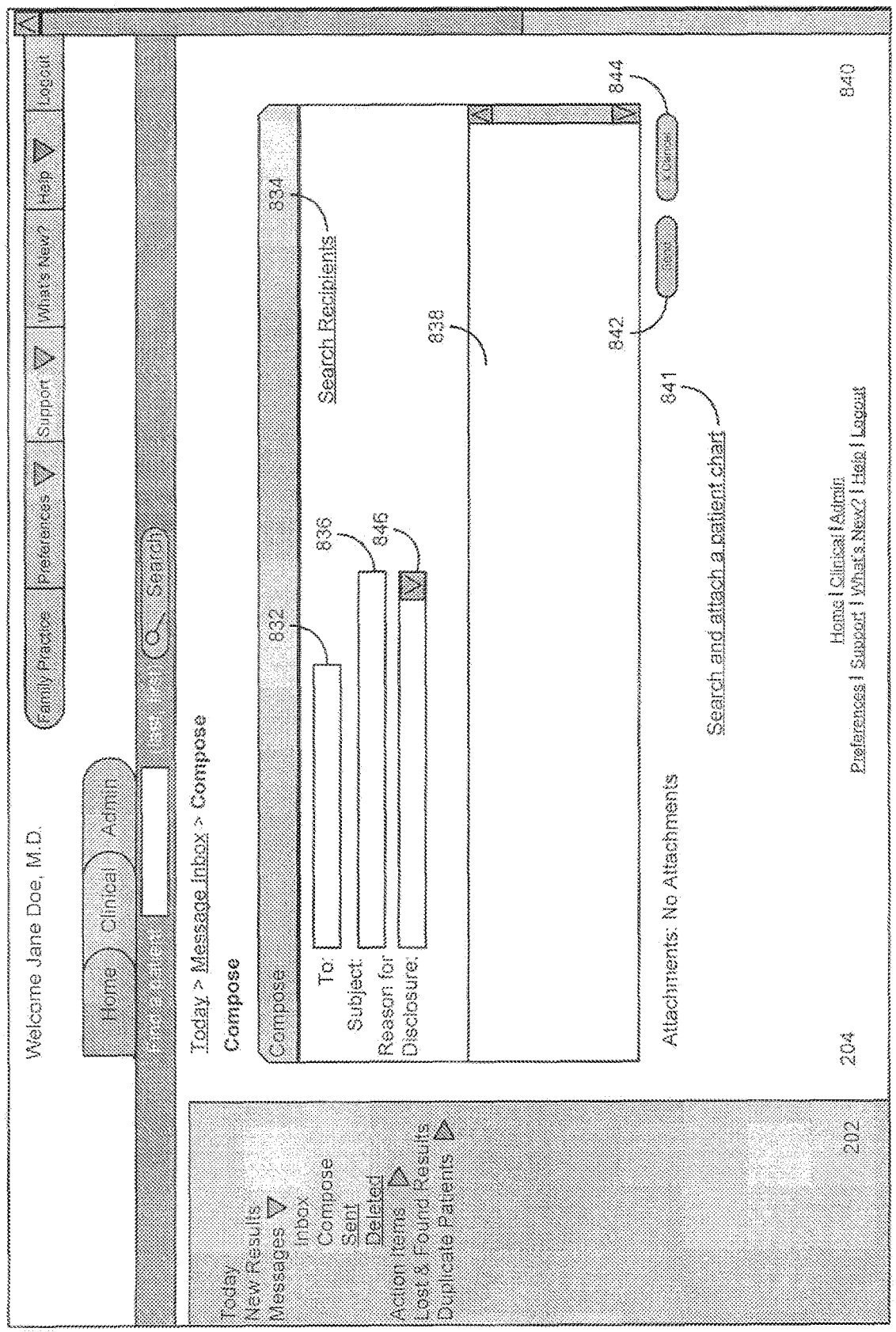
FIG. 15 depicts a user interface display suitable for composing and sending an electronic message according to an embodiment of an EHR system.

The message composition screen 840 of FIG. 15 depicts a user interface display adapted to composing and sending a user message. A text box 832 contains the names of one or more recipients. Depending on the implementation of messaging, recipients' names may or may not be directly entered text box 832.

Recipients may also be entered by following the hyperlink 834 labeled "Search Recipients." The hyperlink 834 may lead to a display (not pictured) allowing entry of one or more criteria to be used to search for potential recipients of the message. The hyperlink 834 may lead also, depending on the EHR system, to a display (not pictured) of the names of one or more recent recipients of user messages. Depending on the EHR system, one or more recipients may be added though either means or both. EHR systems may provide other ways to add recipients in addition to or instead of the ones described here.

Text areas support entry of a subject 836 for the message and the message body 838.

The hyperlink 84 labeled "Search and attach a patient chart" may serve to attach chart data to a message. When followed, the hyperlink 841 may lead to a user interface that supports selecting a patient, such as, for example, the patient selection screen 290 depicted in FIG. 3. In some EHR systems, if message composition was initiated from a screen associated with a patient, such as, e.g., the patient summary screen 360 depicted in FIG. 4, searching for and/or selecting a user may be skipped.

Depending on the EHR system, once a patient has been selected, a screen such as the patient summary screen 360 (FIG. 4) may be displayed. That screen, in turn, may be used to access that patient's chart data. Individual items of data may be selected. Depending on the EHR system, examples of chart data that may be attached comprise laboratory test results prescription information, and/or stored Flowsheets, among many possibilities. Once desired items have been selected, a hyperlink (not pictured) or other means may enable return to the message composition screen 840. Upon return to the message composition screen 840, the selected data items will have been attached to the message. EHR systems may support removal of attached data from a draft message and/or attachment of further data.

The button 842 labeled "Send" allows sending the message, including any attachments. The button 844 labeled "Cancel" allows cancellation of a pending message. An EHR system may also provide means (not pictured) by which a draft of a message may be saved and then sent later, possibly after further revision.

In an embodiment of the invention, the message composition screen 840 may comprise a control 846 for entry of one or more reasons for disclosure of patient information. Such reasons may be legally required or otherwise desirable.

FIG. 16 is a partial representation of an electronic message 862 with attached chart data in an EHR system. The representation uses the eXtensible Markup Language (XML), which is a well-known tool for representing structured data for storage, processing, and/or transfer.

The representation of the message 862 comprises three top-level components. The first top-level component is the header 864, which, depending on the implementation, may comprise information relevant to handling the message, e.g., the sender 866, the recipient 868, and/or the subject 870 of the message, among other things.

The second top-level component is the body 874, which in this illustration contains only the text of the message.

The third top-level component is the attachment element 880, which may comprise zero or more attachments 882. The illustrated representation does not directly represent attached chart data, but instead contains a reference 884 (often called a "pointer") that uniquely refers to a specific entry on a specific patient's chart. The meaning and resolution of references depends on the implementation. One possible meaning (of many) is that the reference 884 is a unique identifier of the record the chart item that appears in one or more tables in a relational database management system. The existence of a unique identifier called a "primary key" is well known in the relevant arts, and some EHR systems may use a representation of a primary key as a reference 884 to chart data.

The XML fragment of FIG. 16 serves primarily to illustrate the data that a message may in some systems comprise, by depicting certain aspects of data associated with a message and one possible representation of those aspects. It will be appreciated that different and/or additional data may be associated with a message and that many other representations are possible, including, for example, differently-structured XML documents and/or representations other than those using a markup language such as XML. For example, a messaging system may store data associated with a message in one or more fields of one or more tables in a relational database management system.

An EHR system may use the reference 884 to identify the item of chart data referred to. This process may be called "dereferencing." Dereferencing a pointer reveals an item of chart data, which the recipient may view. If the item is saved to a patient's chart, an EHR system may duplicate the item and then save the new copy in association with the recipient's version of that patient's chart. Instead of duplicating an item of chart data, an EHR system may give the recipient direct access to the item on the sender's chart.

Some EHR systems may support both options, choosing one or the other based on circumstances. For example, if the sender and recipient are in practice together, they may have access to the same charts. In that case, viewing an attached item of chart data may comprise accessing the shared chart. If the sender and receiver are not in practice together, the recipient may lack privileges to access the sender's chart directly, and the attached chart item may then be duplicated, and the copy saved, as already described.

Figure 17:
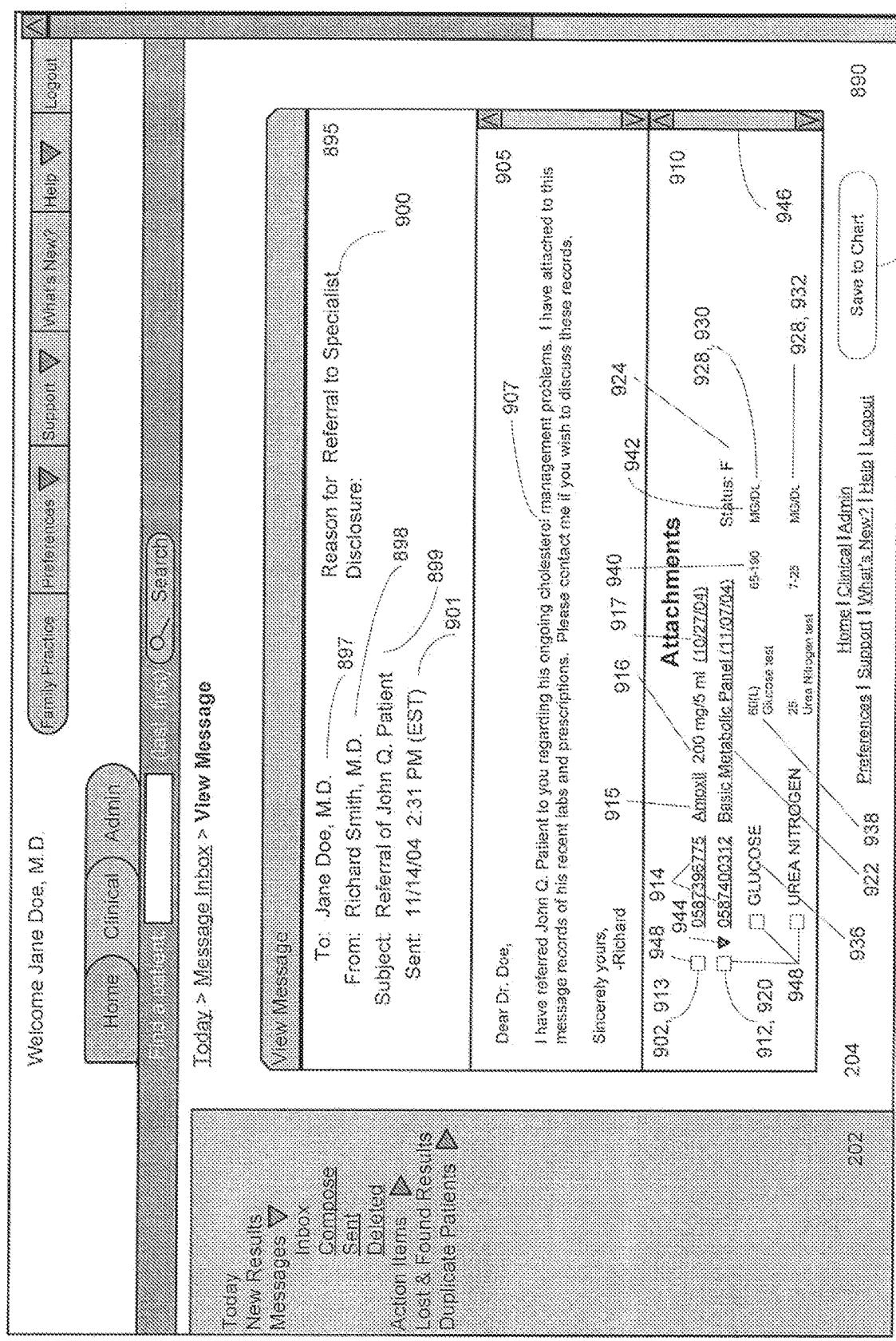
FIG. 17 depicts a user interface display suitable for viewing an electronic message and saving a persistent copy of data attached thereto according to an embodiment of an EHR system.

After an electronic message has been delivered, it may be viewed, and, in some embodiments of the invention, some or all attached data may be viewed and/or saved to a patient's chart. FIG. 17 depicts a user interface display 860 that an EHR system may use to present a message and attached data and to allow the recipient to view attached chart data and possibly to save it.

The message display may be divided into three areas. A header area 870 may display information about the message itself. In an embodiment of this invention, this information may comprise, e.g., the recipient 872 and sender 874; a subject, title, or summary of the message 876; the reason 878 for disclosing the attached patient records (if any) to the recipient; and the time 880 when the message was sent. The header area 870 may display other information in addition or instead of the depicted information.

A body area 890 displays the body 892 of the electronic message. In an implementation of messaging, the body 892 comprises text. In other implementations, the body 892 may comprise images and/or other multimedia content (not pictured) and/or hyperlinks to other data (not pictured).

An attachments area 900 displays information associated with attachments 902, if any, to the electronic message. In the depicted messaging system, each line comprises a summary of information about a single attached chart item. For example, the first displayed chart item is a prescription 904. The display is a summary that comprises an item number 906 that uniquely identifies the chart item within the EHR system, the name 908 of the prescribed drug, the form 910 of the drug, and the date of the prescription 912. One or more of the components of the summary of the prescription 904 may act as hyperlinks to further data (not pictured) related to the chart item.

The next displayed chart item is a panel 920 of laboratory tests. The display is a summary that in the depicted embodiment of the invention comprises an item number 906, the name and date 922 of the test panel, and a code 924 indicating the status of the panel 920. The codes and their meanings depend on the EHR system, but in the depicted embodiment, the code "F" indicates that the status of the test panel 920 is "final," which means that results are available for all tests 928 comprised by the panel 920.

A panel comprises one or more laboratory tests. The panel 920 depicted in FIG. 17 comprises blood tests for glucose 930 and urea nitrogen 932, among others. In the depicted embodiment of the invention, the information for each test comprises the name 936 of the analyte, the value 938 detected by the laboratory, a "reference range" 940, which may represent a range of typical values for the analyte, and the units 942 of measurement in which the data are presented.

The panel 920 may be regarded as a single data item, as may be the prescription 904. But it comprises several tests 928, each of which may itself be regarded as a data item. The panel 920 may therefore be described as a hierarchical data item, and may be viewed either on a single line as a single data item or on multiple lines as an object comprising multiple data items. The triangle 936 is a control that toggles between the two views of the panel 920.

If, as in the depicted user interface display 860, full display of information about the attachments would exceed the available space in the attachments area 900, the attachments area 900 may contain a control 934 supporting scrolling through the displayed list of attachments.

Each data item in the attachments area 900 is associated with a checkbox control 938, by which a user may choose to save that chart item to a chart managed by that user. In a messaging system, selecting a checkbox control 938 next to a hierarchical data item may cause selection of each data item that it comprises. In such a system, the user may then deselect individual data items to exclude them from the chart.

Once the user has selected one or more attached data items, the user may then select the save button 940, causing the system to save a persistent copy of each selected data item to a chart managed by the user. In such a case, a messaging system may first check that the recipient has a chart for the associated patient, and, if not, permit the recipient to create one. Creation of a patient chart by the recipient may in a particular EHR system rely on some or all demographic information present in the sender's version of the patient chart.

The copy is considered a persistent copy because it resides in nonvolatile storage and is not regarded by the system as a temporary file that may be subject to routine deletion.

In creating copies of attached data, a messaging system may not be limited to the one or more data sets that the reference directly specifies. A system may follow references to associated data to create a copy or copies of related data, including data providing semantic data, and to associate these copies with the copy of the directly-referenced data. The system may follow such links to copy associated records to any desired level of indirection. For some associated data, copying the reference to the associated data may suffice.

For example, data for a single test result may be associated with a set of data describing the data sample, a set or data describing the test panel, and/or a set of data related to payment for the test, among many other things. The result data may also be associated with information describing the vendor of laboratory services and/or the specifications for the particular test, again, among many other things. In an EHR system, copying the chart item containing such a test result may therefore comprise, e.g., copying records specific to the test and/or patient, but copying only references to data that does not vary from test to test and/or is not specific to the particular test, panel, and patient.

In making such a copy, an EHR system has access to all data and metadata, including semantic data, that the sender has access to. Such a system may thus preserve any or all such data when copying the data for the recipient.

Implementation of messaging within an EHR system may comprise facilities for managing user messages. Such facilities are well known and may comprise, for example, one or more of: viewing sent or received messages; filtering messages according to one or more criteria; deleting messages, replying to messages, forward messages to other users; sending messages via fax; searching and/or retrieving stored messages; and/or other facilities.

I claim:

1. A computerized method of presenting information graphically, comprising:
   presenting on an electronic display device a flowsheet, comprising:
     a plurality of identifiers, each of which textually identifies exactly one of at least a plurality of stored series of one or more related data points, wherein each data point comprises a value and temporal information, the temporal information comprising a time, a date, or a time and a date, each of the identifiers being displayed in association with one or more controls, the associated controls together permitting a user to chose between associating the series with a left axis, associating the series with a right axis, and associating the series with no axis;
     a plurality of temporal labels, each temporal label indicating at least a time, a date, or a time and a date, the temporal labels together spanning a period of time;
     a plurality of numeric values, each numeric value representing one or more data points from a respective exactly one of the plurality of stored series, each numeric value being displayed in visual association with the identifier that identifies the respective series from which the data points were taken, each numeric value further being displayed in visual association with exactly one of the temporal labels, no more than one of the numeric values that are associated with a respective identifier being associated with any respective temporal label; and
     a zoom control configured to allow a user to modify the period of time spanned by the temporal labels;
   in response to input from a user, selecting a first one or more of the plurality of identifiers and, for each of the first one or more of the plurality of identifiers, associating the respective series associated with the identifier with the left axis or the right axis;
   in response to input from a user, selecting a second one or more of the plurality of identifiers;
   in response to input from the user, presenting on the electronic display device a graphical display that comprises:
     a first graph that comprises a first horizontal axis indicating a time interval; a first left vertical axis indicating a first range of values; a first right vertical axis indicating a second range of values; and at least one set of symbols, each set comprising at least one symbol that corresponds to at least one of the data points comprised by the stored series represented by one of the first selected one or more identifiers; wherein the horizontal placement of each symbol indicates the temporal information associated with the corresponding data point, the vertical placement of each symbol indicates the value associated with the corresponding data point, and, for each set of symbols comprised by the first graph, all symbols within the set correspond to data points comprised by the same stored series; and
     a second graph that comprises a second horizontal axis indicating a time interval; a second vertical axis indicating a third range of values; and at least one set of symbols, each set comprising at least one symbol that corresponds to at least one of the data points comprised by stored series represented by one of the second selected one or more identifiers; wherein the horizontal placement of each symbol indicates the temporal information associated with the corresponding data point, the vertical placement of each symbol indicates the value associated with the corresponding data point, and, for each set of symbols comprised by the second graph, all symbols within the set correspond to data points comprised by the same stored series;
   wherein:
     at least one of the numeric values is a derived numeric value that represents two or more of the data points and is calculated based on one or more of the values of the represented data points;
     the first graph is presented adjacent to the second graph and either above it or below it; and
     the first horizontal axis and the second horizontal axis are aligned vertically so that any position indicating a time relative to the first horizontal axis indicates the same time relative to the second horizontal axis.

2. The computerized method of claim 1, wherein the derived numeric value is an average of the values of the represented data points.

3. A computer system programmed to perform a method of presenting information graphically, the method comprising:
presenting on an electronic display device a flowsheet, comprising
a plurality of identifiers, each of which textually identifies exactly one of at least a plurality of stored series of one or more related data points, wherein each data point comprises a value and temporal information, the temporal information comprising a time, a date, or a time and a date, each of the identifiers being displayed in association with one or more controls, the associated controls together permitting a user to choose between associating the series with a left axis, associating the series with a right and associating the series with no axis;
a plurality of temporal labels, each temporal label indicating at least a time, a date, or a time and a date, the temporal labels together spanning a period of time;
a plurality of numeric values, each numeric value representing one or more data points from a respective exactly one of the plurality of stored series, each numeric value being displayed in visual association with the identifier that identifies the respective series from which the data points were taken, each numeric value further being displayed in visual association with exactly one of the temporal labels, no more than one of the numeric values that are associated with a respective identifier being associated with any respective temporal label; and
a zoom control configured to allow a user modify the period of time spanned by the temporal labels;
in response to input from a user, selecting a first one or more of the plurality of identifiers and, for each of the first one or more of the plurality of identifiers, associating the respective series associated with the identifier with the left axis or the right axis;
in response to input from a user; selecting a second one or more of the plurality of identifiers;
in response to input from the user, presenting on the electronic display device a graphical display that comprises:
a first graph that comprises a first horizontal axis indicating a time interval; a first left vertical axis indicating a first range of values; a first right vertical axis indicating a second range of values; and at least one set of symbols, each set comprising at least one symbol that corresponds to at least one of the data points comprised by the stored series represented by one of the first selected one or more identifiers; wherein the horizontal placement of each symbol indicates the temporal information associated with the corresponding data point, the vertical placement of each symbol indicates the value associated with the corresponding data point, and, for each set of symbols comprised by the first graph, all symbols within the set correspond to data points comprised by the same stored series; and
a second graph that comprises a second horizontal axis indicating a time interval; a second vertical axis indicating a third range of values; and at least one set of symbols, each set comprising at least one symbol that corresponds to at least one of the data points comprised by the stored series represented by one of the second selected one or more identifiers; wherein the horizontal placement of each symbol indicates the temporal information associated with the corresponding data point, the vertical placement of each symbol indicates the value associated with the corresponding data point; and, for each set of symbols comprised by the second graph, all symbols within the set correspond to data points comprised by the same stored series;
wherein:
at least one of the numeric values is a derived numeric value that represents two or more of the data points and is calculated based on one or more of the values of the represented data points;
the first graph is presented adjacent to the second graph and either above it or below it; and
the first horizontal axis and the second horizontal axis are aligned vertically so that any position indicating a time relative to the first horizontal axis indicates the same time relative to the second horizontal axis.

4. The computerized method of claim 3, wherein the derived numeric value is an average of the values of the represented data points.

5. A computer program product comprising a computer-readable storage medium, other than a transitory propagating signal, encoded with instructions that, when executed within a computer system, cause the computer system to perform a method of presenting information graphically, the method comprising:
presenting on an electronic display device a flowsheet, comprising
a plurality of identifiers, each of which textually identifies exactly one of at least a plurality of stored series of one or more related data points, wherein each data point comprises a value and temporal information, the temporal information comprising a time, a date, or a time and a date, each of the identifiers being displayed in association with one or more controls, the associated controls together permitting a user to choose between associating the series with a left axis, associating the series with a right axis, and associating the series with no axis;
a plurality of temporal labels, each temporal label indicating at least a time, a date, or a time and a date, the temporal labels together spanning a period time;
a plurality of numeric values, each numeric value representing one or more data points from a respective exactly one of the plurality of stored series, each numeric value being displayed in visual association with the identifier that identifies the respective series from which the data points were taken, each numeric value further being displayed in visual association with exactly one of the temporal labels, no more than one of the numeric values that are associated with a respective identifier being associated with any respective temporal label; and
a zoom control configured to allow a user to modify the period of time spanned by the temporal labels;
in response to input from a user, selecting a first one or more of the plurality of identifiers and, for each of the first one or more of the plurality of identifiers, associating the respective series associated with the identifier with the left axis or the right axis;
in response to input from a user, selecting a second one or more of the plurality of identifiers;

in response to input from the user, presenting on the electronic display device a graphical display that comprises:
- a first graph that comprises a first horizontal axis indicating a time interval; a first left vertical axis indicating a first range of values; a first right vertical axis indicating a second range of values; and at least one set of symbols, each set comprising at least one symbol that corresponds to at least one of the data points comprised by the stored series represented by one of the first selected one or more identifiers; wherein the horizontal placement of each symbol indicates the temporal information associated with the corresponding data point, the vertical placement of each symbol indicates the value associated with the corresponding data point, and, for each set of symbols comprised by the first graph, all symbols within the set correspond to data points comprised by the same stored series; and
- a second graph that comprises a second horizontal axis indicating a time interval; a second vertical axis indicating a third range of values; and at least one set of symbols, each set comprising at least one symbol that corresponds to at least one of the data points comprised by the stored series represented by one of the second selected one or more identifiers; wherein the horizontal placement of each symbol indicates the temporal information associated with the corresponding data point, the vertical placement of each symbol indicates the value associated with the corresponding data point, and, for each set of symbols comprised by the second graph, all symbols within the set correspond to data points comprised by the same stored series;

wherein:
- at least one of the numeric values is a derived numeric value that represents two or more of the data points and is calculated based on one or more of the values of the represented data points;
- the first graph is presented adjacent to the second graph and either above it or below it; and
- the first horizontal axis and the second horizontal axis are aligned vertically so that any position indicating a time relative to the first horizontal axis indicates the same time relative to the second horizontal axis.

6. The computerized method of claim 5, wherein the derived numeric value is an average of the values of the represented data points.

* * * * *